(12) United States Patent
Yadan et al.

(10) Patent No.: US 10,308,602 B2
(45) Date of Patent: Jun. 4, 2019

(54) ORGANOSELENIUM COMPOUNDS, METHOD FOR PRODUCING SAME, AND PHARMACEUTICAL USES THEREOF IN PARTICULAR AS ANTITUMOR AGENTS

(71) Applicant: TETRAHEDRON, Paris (FR)

(72) Inventors: Jean-Claude Yadan, Paris (FR); Irene Erdelmeier, Paris (FR); Marc Moutet, Paris (FR); Remi Lebel, Paris (FR)

(73) Assignee: TETRAHEDRON, Paris (FR)

( * ) Notice: Subject to any disclaimer, the term of this patent is extended or adjusted under 35 U.S.C. 154(b) by 0 days.

(21) Appl. No.: 15/302,633

(22) PCT Filed: Apr. 7, 2015

(86) PCT No.: PCT/FR2015/050886
§ 371 (c)(1),
(2) Date: Oct. 7, 2016

(87) PCT Pub. No.: WO2015/155453
PCT Pub. Date: Oct. 15, 2015

(65) Prior Publication Data
US 2017/0114011 A1 Apr. 27, 2017

(30) Foreign Application Priority Data
Apr. 8, 2014 (FR) .................................... 14 53136

(51) Int. Cl.

| | | |
|---|---|---|
| C07C 391/00 | (2006.01) |
| A61K 31/16 | (2006.01) |
| A61K 31/19 | (2006.01) |
| A61K 31/22 | (2006.01) |
| A61K 31/235 | (2006.01) |
| A61K 31/265 | (2006.01) |
| A61K 31/198 | (2006.01) |
| A61K 31/223 | (2006.01) |
| A61K 31/23 | (2006.01) |
| A61K 31/231 | (2006.01) |
| A61K 31/27 | (2006.01) |
| A61K 31/40 | (2006.01) |
| A61K 31/4164 | (2006.01) |
| A61K 31/4406 | (2006.01) |
| A61K 31/4453 | (2006.01) |
| A61K 31/5375 | (2006.01) |
| A61K 45/06 | (2006.01) |
| C07D 213/80 | (2006.01) |
| C07D 233/90 | (2006.01) |
| C07D 295/195 | (2006.01) |

(52) U.S. Cl.
CPC ............ *C07C 391/00* (2013.01); *A61K 31/16* (2013.01); *A61K 31/19* (2013.01); *A61K 31/198* (2013.01); *A61K 31/22* (2013.01); *A61K 31/223* (2013.01); *A61K 31/23* (2013.01); *A61K 31/231* (2013.01); *A61K 31/235* (2013.01); *A61K 31/265* (2013.01); *A61K 31/27* (2013.01); *A61K 31/40* (2013.01); *A61K 31/4164* (2013.01); *A61K 31/4406* (2013.01); *A61K 31/4453* (2013.01); *A61K 31/5375* (2013.01); *A61K 45/06* (2013.01); *C07D 213/80* (2013.01); *C07D 233/90* (2013.01); *C07D 295/195* (2013.01); *C07C 2601/02* (2017.05); *C07C 2603/18* (2017.05)

(58) Field of Classification Search
CPC combination set(s) only.
See application file for complete search history.

(56) References Cited

FOREIGN PATENT DOCUMENTS

CN 102655745 9/2012

OTHER PUBLICATIONS

Abbas, M. et al. "One pot synthesis of selenocysteine containing peptoid libraries by Ugi multicomponent reactions in water" Chem. Commun., 2006, 541-543.*
"ACS" "Can Cancer Be Prevented?" (www.cancer.org) Feb. 24, 2009, p. 1. (Year: 2009).*
Padayaty, S.J. et al. "Intravenously administered vitamin C as cancer therapy: three cases" CMAJ 2006, 174 (7), 937-942.*
Suggitt, M. et al. "50 Years of Preclinical Anticancer Drug Screening: Empirical to Target-Driven Approaches" Clin Cancer Res 2005, 11, 971-981 (Year: 2005).*
Yusuf, R.Z. et al. "Paclitaxel Resistance: Molecular Mechanisms and Pharmacologic Manipulation" Current Cancer Drug Targets, 2003, 3, 1-19 (Year: 2003).*
Sausville, E.A. et al. "Contributions of Human Tumor Xenografts to Anticancer Drug Development" Cancer Res 2006; 66: (7), 3351-3354 (Year: 2006).*
Ouerdane, L. et al. "Comprehensive speciation of low-molecular weight selenium metabolites in mustard seeds using HPLC—electrospray linear trap/orbitrap tandem mass spectrometry" Metallomics, 2013, 5, 1294—1304 (Year: 2013).*
Patani, G.A. et al. "Bioisosterisnn: A Rational Approach in Drug Design" Chem. Rev. 1996, 96, 3147-3176 (Year: 1996).*
Bhattacharya, A. et al. "Inhibition of Colon Cancer Growth by Methylselenocysteine—induced Angiogenic Chemomodulation is influenced by Histological Characteristics of the Tumor" Clin Colorectal Cancer. Jul. 2009; 8(3): 155 (pp. 1-17) (Year: 2009).*

(Continued)

*Primary Examiner* — Andrew S Rosenthal
(74) *Attorney, Agent, or Firm* — Clark & Brody

(57) ABSTRACT

The invention relates to a selenium compound. Said selenium compound has formula (I), where $R^1$=alkyl; $R^2$=H, $R^4C(=O)$, $R^4OC(=O)$, a-aminoacyl, $CH_3SeCH_2CH_2CH(NH_2)C(=O)$, $CH_3SeCH_2CH_2CH(OH)C(=O)$; X=OH, $OR^3$, $NH_2$, $NR^4R^5$, α-amino acid, $CH_3SeCH_2CH_2CH(COOH)NH-$, $CH_3SeCH_2CH_2CH(COOH)0-$; $R^3$=alkyl; $R^4$=alkyl, aryl; $R^5$=H, alkyl, aryl; $R^4$ and $R^5$ which can together form a 5- or 6-membered cycloalkyl radical which can comprise a heteroatom; provided that when X=NH-terbutyl, $R^2 \neq C(=O)CH_3$. Said compound can be used as a pharmaceutical substance, in particular as an antitumour substance.

23 Claims, 3 Drawing Sheets

(56) References Cited

OTHER PUBLICATIONS

Patani, G.A. et al. "Bioisosterism: A Rational Approach in Drug Design" Chem. Rev. 1996, 96, 3147-3176 (Year: 1996).*
Padayaty, S.J. et al. "Intravenously administered vitamin C as cancer therapy: three cases" CMAJ 2006, 174 (7), 937-942 (Year: 2006).*
Cao, S. et al. "Selective Modulation of the Therapeutic Efficacy of Anticancer Drugs by Selenium Containing Compounds against Human Tumor Xenografts" Clin Cancer Res 2004, 10, 2561-2569 (Year: 2004).*
Abbas, M. et al. "One pot synthesis of selenocysteine containing peptoid libraries by Ugi multicomponent reactions in water" Chem. Commun., 2006, 541-543 (Year: 2006).*
Bhattacharya, A. et al. "Inhibition of Colon Cancer Growth by Methylselenocysteine—induced Angiogenic Chemomodulation is influenced by Histological Characteristics of the Tumor" Clin Colorectal Cancer. Jul. 2009; 8(3): 1-17. (Year: 2009).*
Saad Shaaban et al., "Novel peptidomimetic . . . anticancer agents", European Journal of Medicinal Chemistry, vol. 58, Dec. 1, 2012, pp. 192-205.
Muhammad Abbas et al., "One pot synthesis . . . reactions in water", Chemical Communications, No. 5, Jan. 1, 2006, p. 541.
Dong et al., "Evidence of a . . . by Methylseleninic Acid", Anticancer Research 22: 27-32 (2002).
Papp et al., "From Selenium to . . . in Human Health", Antioxidants & Redox Signaling, vol. 9, No. 7, 2007.
Whanger, "Selenium and its relationship to cancer: an update", British Journal of Nutrition, (2004), 91, 11-28.
Medina et al., "Se-Methylselencysteine: A New . . . Breast Cancer", Nutrition and Cancer, 40(1), 12-17, 2001.
Ip et al., "New concepts in selenium chemoprevention", Cancer and Metastasis Reviews 21: 281-289, 2002.
Suzuki et al., "Differential apoptotic . . . organoselenium compounds", Cancer Chemother Pharmacol, (2010) 66:475-484.
Hu et al., "PKB/AKT and ERK . . . prostate cancer cells", Carcinogenesis, vol. 26, No. 8, pp. 1374-1381, 2005.
Wang et al., "Methyl-Selenium Compounds . . . with Survival Benefit", May 2009.
Ip et al., "In Vitro and In Vivo . . . for Cancer Chemoprevention", Cancer Reasearch 60, 2882-2886, Jun. 1, 2000.
Li et al., "Superior in vivo . . . selenomethionine or selenite", Cacinogenesis, vol. 29, No. 5, pp. 1005-1012, 2008.
Wu et al., "Endoplasmic Reticulum . . . Selenium Action", Departments of Cancer Chemoprevention and Cellular Stress Biology, 2005.
Sinha et al., "Abstract B117: Methylselenic acid . . . cells in vitro", Cancer Prevention Research, 2008.
Yan et al., "Dietary supplementation . . . carcinoma in mice", International Journal of Cancer, 2012.
SubbaRao V. Madhunapantula et al., "PBISe, a novel selenium-containing . . . of malignant melanoma", Mol Cancer Ther., 2008.
Chen et al., "Inhibition of Nuclear . . . of the p50 Subunit", Cancer Research 67, (21), Nov. 1, 2007.
Sharma et al., "Targeting Akt3 Signaling . . . Using Isoselenocyanates", Cancer Therapy: Preclinical, 2009.

* cited by examiner

Figure 1: Diagram of the process of synthesis of the compounds according to general formula (I)
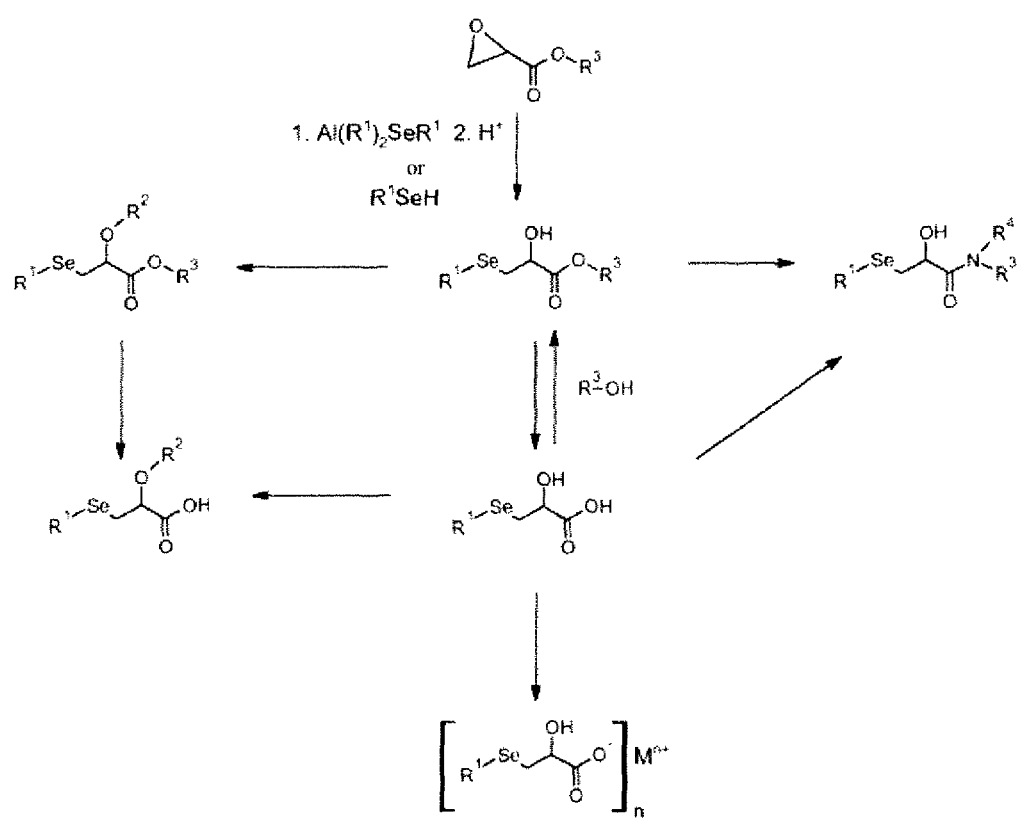

Figure 2: Viability percentage of cells DU145 and LS174T versus the concentration of compound 4, after 96 hours of treatment
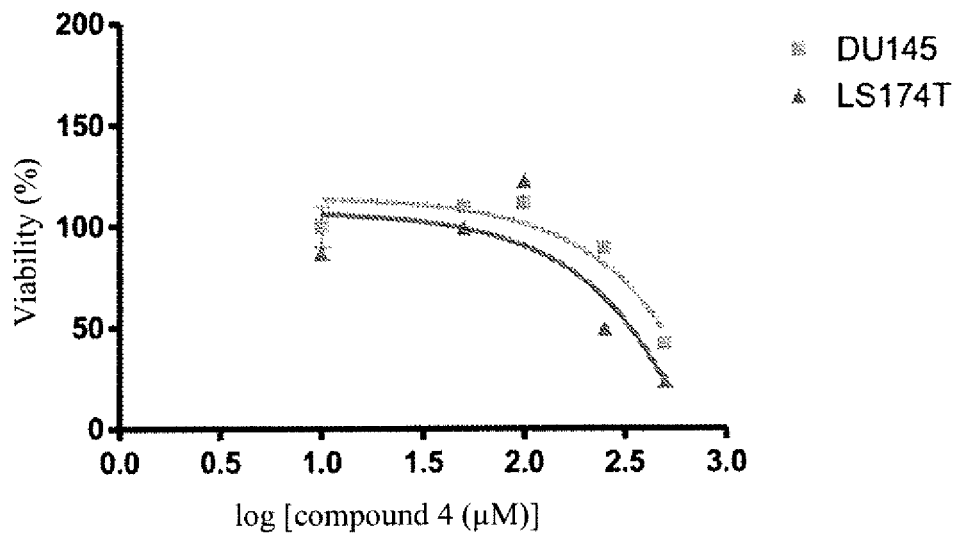
Figure 3: Viability of cells DU145, LS174T and HT-29 versus the concentration of compound 10, after 96 hours of treatment
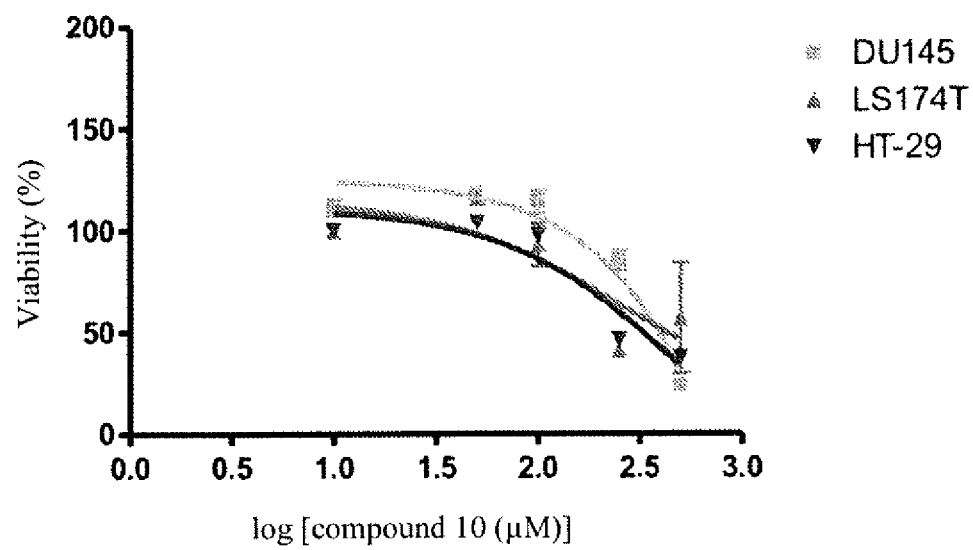

Figure 4: Viability percentage of cells PC3, DU145, PANC-1 and MIA PaCa-2 versus the concentration of compound 38, after 96 hours of treatment
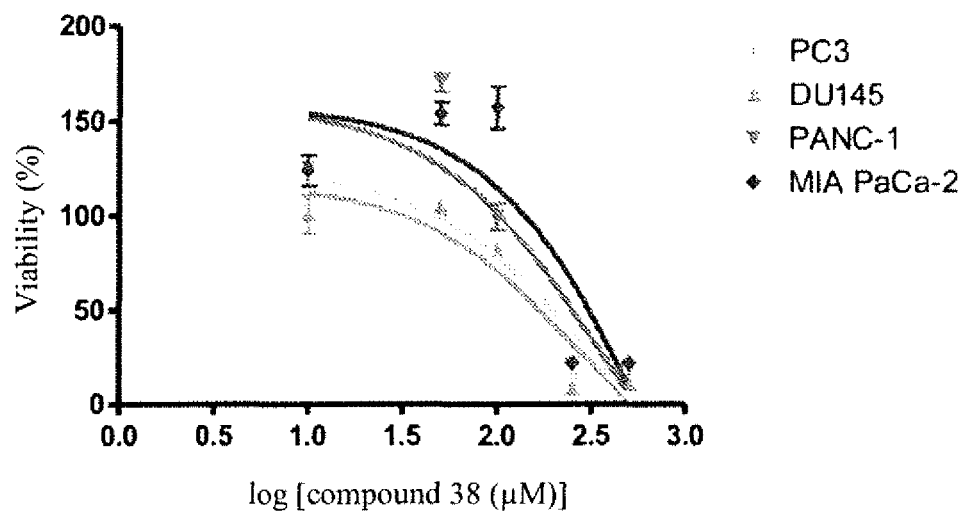
Figure 5: Viability percentage of cells HT-29, LS174T, HepG2 and MCF-7 versus the concentration of compound 38, after 96 hours of treatment
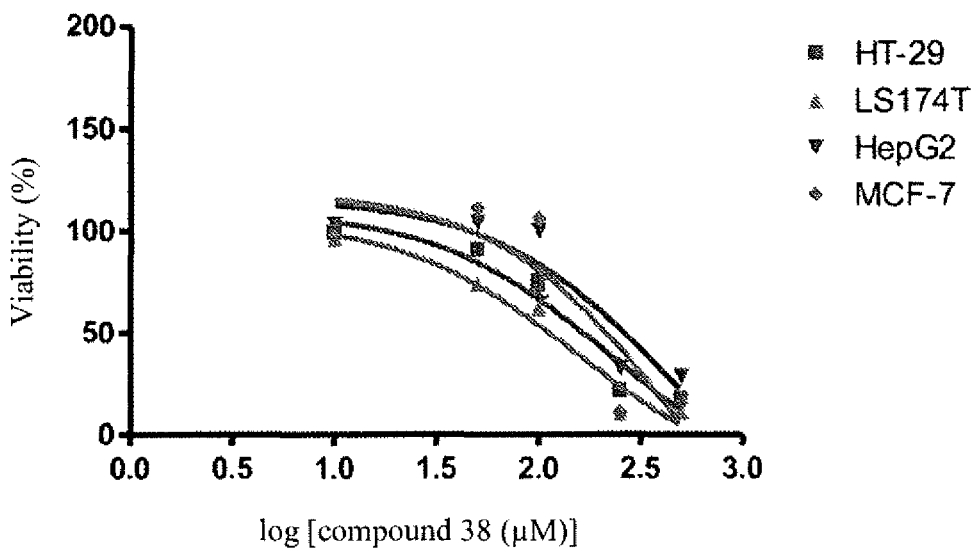

ORGANOSELENIUM COMPOUNDS, METHOD FOR PRODUCING SAME, AND PHARMACEUTICAL USES THEREOF IN PARTICULAR AS ANTITUMOR AGENTS

The present invention relates to:
novel organoselenium compounds;
methods for preparing same;
the use thereof as pharmaceutical active ingredient;
and pharmaceutical compositions containing them, in particular as novel antitumor agents.

PRIOR ART

This invention relates to novel organoselenium compounds, to the method for preparing same, to the use thereof as pharmaceutical active ingredient, as well as to pharmaceutical compositions containing them, in particular as novel antitumor agents. More particularly, this invention relates to the preparation of organoselenium compounds that include 2-hydroxy-3-methylselenopropanoic acid, the salts thereof as well as the esters and amides derived from 2-hydroxy-3-methylselenopropanoic acid, having pharmaceutical activity and in particular antitumor or anticancer activity, alone or in combination with other pharmaceutical agents and in particular antitumor agents.

Cancer remains one of the main causes of death in the industrialized countries. In spite of numerous advances in the development of new anticancer therapies, a curative treatment is still a real need for the majority of solid tumors. The antitumor potential of "selenium" was identified at the end of the 1960s following studies revealing lower rates of mortality due to cancer in certain regions where the soil was rich in inorganic selenium. Over the last twenty years, in the context of animal experimentation, numerous studies have revealed the anticancer activity of "selenium" in a certain number of organs [Papp L V et al., 2007, Antioxid Redox Signal, 9:775]. Out of a total of eight clinical trials for evaluation of the effect of "selenium" on the incidence of cancers, seven ended up with positive results [Whanger P D, 2004, Br. J. Nutr., 91(1):11]. This confirms the numerous studies conducted in animals.

The antitumor activity of methylselenocysteine (MeSeCys) was observed by Ip et al. at the beginning of the 2000s [Medina D et al., 2001, Nutrition and Cancer, 40(1): 12]. In order to be effective, MeSeCys must be "activated" into methylselenol by β-lyase [Ip C. et al., 2002 Cancer & Metast. Rev., 21(3-4):281]. The human tumor cells of breast or prostate cancer exhibit a low level of β-lyase activity, which leads to a low sensitivity of these tumor cells to physiologically acceptable concentrations of MeSeCys. In contrast, daily doses of 3 mg selenium equivalent/kg (Se eq./kg) of MeSeCys administered for 18 to 26 weeks to transgenic mice with a prostate adenoma slow down progress of the tumor lesions, increase apoptosis and reduce proliferation of the tumor cells [Wang L et al., 2009, Cancer Prev. Res., 2:484].

MeSeCys induces apoptosis of the carcinoma cells by activation of the caspase pathway [Suzuki M. et al., 2010, Cancer Chemother. Pharmacol., 66(3):475]. MeSeCys inhibits the growth of mammary cells, and it induces apoptosis according to a caspase-dependent mechanism and involves the release of mitochondrial cytochrome C as well as the fragmentation of the nucleosomal DNA [Hu H et al., 2005, Carcinogenesis, 26:1374]. This same compound inhibits the progress of prostate cancer in a murine model and increases the survival of the mice [Wang L et al., 2009, Cancer Prev. Res., 2:484].

MeSeCys is not easy to synthesize and moreover requires metabolic activation in order to be effective.

Methylseleninic acid (MSA) has been used for its capacity to generate methylselenol $CH_3SeH$ after reduction by biological reducing agents such as intracellular glutathione. This gives it an anticancer activity that has been demonstrated to be higher than that of MeSeCys [Ip C et al., 2000, Cancer Res., 60:2882] and higher than that of selenomethionine [Li G X et al., 2008, Carcinogenesis, 29:1005]. MSA is capable of modulating several specific biomarkers, resulting in a reduction of cell proliferation and an activation of apoptosis [Dong Y. et al., 2002, Anticancer Res., 22:27]. It induces a stress at the site of the endoplasmic reticulum by oxidation of the protein thiols, leading to abnormal folding of the latter. If the repair system is "overwhelmed," then the cell engages in an apoptotic process [Wu Y et al., 2005, Cancer Res., 65(19):9073]. Furthermore, MSA reduces, in a dose-dependent manner, the level of hypoxia-inducible factor HIF-1α in hormone-independent prostate adenoma cells [Sinha R et al., 2008, Cancer Prev. Res., 1, 7, Suppl., abstract No. B117]. MSA reduces the spontaneous metastases of cancerous lung cells in mice [Yan L et al., 2011, Int. J. Cancer, 131:1260]. MSA, although very active, is difficult to use as a drug active ingredient for obvious reasons connected with the formulation and the stability thereof.

Finally, other organoselenium compounds have been described as having anticancer properties, such as S,S'-1,4-phenylenebis(1,2-ethanediyl)-isoseleno-urea (SubbaRao V M et al., 2008, Mol. Cancer Ther., 7(5):1297], 1,4-phenylenebis(methylene)-selenocyanate [Chen K M, 2007, Cancer Res., 67(21):10475] as well as a series of isoselenocyanates [Sharnna A, 2009, Clin. Cancer Res., DOI 10.1158/1078-0432]. For the same reasons as for MSA, these compounds are very difficult to use as drugs.

The SHAABAN document, in the European Journal of Medicinal Chemistry, 58, (2012), P192-205, describes various compounds containing redox active chalcogens and quinones as potential anticancer agents. On page 195, SHAABAN describes compounds where R1 could include an aromatic ring (which could be an aryl) and R2=C(=O) R4 and R4O(C=O) which have a similarity to R4=aryl of the compounds of formula (I) of the present invention described below.

However, in the compounds of formula (I) of the present invention described below, an aromatic ring is provided only in the second position that is to say in alkyl-aryl form with alkyl attached to the selenium.

Consequently, the compounds of formula (I) are novel with respect to compounds 4 to 18, page 195 of SHAABAN.

Furthermore, for compounds 4, 5, 7, 10 and 11 of SHAABAN which have a NH-tert-butyl group corresponding to X of formula (I) of the present invention, the compounds of formula (I) of the present invention are moreover different because in this case R2 is ≠C(=O) $CH_3$ and also R2 is only alkyl or aryl.

Also, the compounds of formula (I) have no quinone type redox group.

Furthermore, the ABBAS document, published in www.rsc.org/chemcomm, Royal Society of Chemistry, 2006, P541-543, describes various compounds that do not have anticancer activity, among which a compound 7t on page 542 that has a methyl substitution on Se corresponding to R1 of formula (I) of the present invention described below.

Nevertheless, the substituent at the top of formula 7t corresponds to the substituent X of formula (I) of the present invention described below, but the definition given provides, for X=alpha-amino acid, a radical of type —NHCH(Y)COOH (alpha-amino acid) which excludes the radical —NH—(CH2)5-COOBn (epsilon-amino acid) of compound 7t of ABBAS.

Moreover, the substituent at the bottom of formula 7t=—O—C(═O)—CH2-NH—C(═O)—O-tert-butyl corresponds to the substituent —O—R2 when R2=R4(C═O), but R4=alkyl or aryl in the context of the present invention.

And the correctly interpreted definition of "alkyl" of the present invention described below provides a substitution in particular by an amino and/or acid or ester group but not a function NH—C(═O)—O—R which would make it possible to correspond to 7t described in ABBAS.

Thus, the definition of alkyl in formula (I) of the present invention does not cover compound 7t of ABBAS.

For the reasons disclosed above, the products of the prior art having anticancer properties are not satisfactory as antitumor agents.

AIMS OF THE INVENTION

One of the aims of the present invention is to design novel organoselenium compounds that are easy to synthesize and formulate.

Another of the aims of the present invention is to prepare these novel organoselenium compounds that can be synthesized in large quantity by methods that can be used on the industrial scale.

Another of the aims of the present invention is to prepare novel organoselenium compounds that are easy to formulate as pharmaceutically active agents and in particular as antitumor or anticancer agents.

Another of the aims of the present invention is to prepare novel pharmaceutical compositions containing at least one of these novel organoselenium compounds, alone or in combination with another antitumor or anticancer agent.

These aims are achieved thanks to the present invention which is based on the design and preparation of novel organoselenium compounds and esters and amides thereof as well as the pharmaceutical uses thereof as antitumor agents. This has been exemplified in the present invention.

DESCRIPTION OF THE INVENTION

The present invention thus aims:

1) to solve the new technical problem consisting in providing novel organoselenium compounds and ester and amide derivatives thereof thus constituting active ingredients of pharmaceutical compositions;

2) to solve this new technical problem according to a solution that includes a method that can be used on the industrial scale for preparation of these novel organoselenium compounds and ester and amide derivatives thereof;

3) to propose pharmaceutical compositions of these organoselenium compounds having general formula (I) alone or in combination with other pharmaceutical agents, in particular with other antitumor agents.

The technical problems listed above are solved for the first time simultaneously by the present invention, in a very easy and economical manner, the method for preparing said novel compounds being very simple to implement while providing good yields.

According to its first aspect, the present invention relates to novel organoselenium agents having the following general formula (I):

GENERAL FORMULA (I)

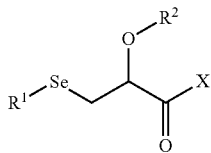

where
R$^1$=alkyl;
R$^2$=H, R$^4$C(═O), R$^4$OC(═O), α-aminoacyl, CH$_3$SeCH$_2$CH$_2$CH(NH$_2$)C(═O), CH$_3$SeCH$_2$CH$_2$CH(OH)C(═O);
X=OH, OR$^3$, NH$_2$, NR$^4$R$^5$, α-amino acid, CH$_3$SeCH$_2$CH$_2$CH(COOH)NH—, CH$_3$SeCH$_2$CH$_2$CH(COOH)O—;
R$^3$=alkyl;
R$^4$=alkyl, aryl;
R$^5$=H, alkyl, aryl;
R$^4$ and R$^5$ being capable of forming together a 5- or 6-membered cycloalkyl radical which can comprise a heteroatom;
provided that, when X=NH-tert-butyl, R$^2$≠C(═O)CH$_3$.

The invention includes all the stereoisomers, diastereoisomers and enantiomers in particular with respect to the carbon atom bearing the group OR$^2$, as well as with respect to the radicals R$^1$ to R$^5$, as well as all oligomers (dimers, trimers, . . . ) and polymers, linear or branched, acyclic or cyclic, obtained between two or more molecules of derivatives of formula (I) described in the invention by esterification reaction between the alcohol and carboxylic acid functions present if applicable, considered alone or in a mixture.

It also includes all the salts of pharmaceutically acceptable acids or bases of said compounds of general formula (I), as well as the sodium, calcium, zinc and magnesium salts.

Among the compounds of general formula (i), the invention in particular relates to:

those characterized in that R$^1$ represents a methyl, ethyl or allyl group;

those characterized in that R$^2$ is selected from the group consisting of H, α-aminoacyls, CH$_3$SeCH$_2$CH$_2$CH(OH)C(═O), R$_4$(C═O), R$_4$O(C═O);

those characterized in that X is selected from the group OH, α-amino acid, CH$_3$SeCH$_2$CH$_2$CH(COOH)NH—, CH$_3$SeCH$_2$CH$_2$CH(COOH)O—;

those characterized in that R$^1$ represents a methyl, ethyl, allyl group; R$^2$ represents R4(C═O), R4O(C═O), and X represents OH or OR3.

those prepared in the experimental part, in particular compounds 4, 10, 38, 46 and 48.

Among the pharmaceutically acceptable acids, it is possible to mention on a non-limiting basis the mineral acids such as comprising hydrochloric, hydrobromic, hydroiodic, sulfuric, and phosphoric acids, or selected from organic acids comprising formic, acetic, trifluoroacetic, propionic, tartaric, benzoic, maleic, fumaric, succinic, citric, oxalic, glyoxylic, and aspartic acids, alkanesulfonic acids comprising methanesulfonic, trifluoromethanesulfonic, and ethanesulfonic, and arylsulfonic acids comprising benzene- and paratoluenesulfonic acids.

Among the pharmaceutically acceptable bases, it is possible to mention on a non-limiting basis the mineral bases such as sodium, lithium, calcium, potassium, magnesium, ammonium or zinc hydroxide, the carbonates of alkali metals or alkaline earth metals such as sodium, lithium, calcium, potassium, magnesium, ammonium or zinc carbonates and bicarbonates, or organic bases such as methylamine, propylamine, trimethylamine, diethylamine, triethylamine, N,N-dimethylethanolamine, tris(hydroxymethyl) aminomethane, ethanolamine, pyridine, picoline, dicyclohexylamine, morpholine, proceine, lysine, arginine, histidine, N-methylglucamine, or else the phosphonium salts such as the alkyl phosphonium salts, the aryl phosphonium salts, the alkyl aryl phosphonium salts, the alkenyl aryl phosphonium salts, or the quaternary ammonium salts such as the tetra-n-butyl-ammonium salts.

In formula (I) above:
alkyl is understood to be a linear, branched or cyclic saturated carbon containing radical with 1 to 26 carbon atoms, which can be substituted by one or more fluorine atoms, or which can be substituted by one or more carbon-carbon double bonds, or which can be substituted by at least one OH group or by at least one amino group, or by at least one COOH or COOR$^6$ group, R$^6$ being a group also selected from a linear, branched or cyclic, saturated or unsaturated carbon containing radical with 1 to 26 carbon atoms which is unsubstituted, such as methyl, ethyl, isopropyl, for example, or which can be substituted by one or more fluorine atoms, such as trifluoromethyl, for example, or which can be substituted by a phenyl group such as benzyl, for example, or which can be substituted by an allyl radical such as linoleyl, linolenyl, palmitoyl, allyl, for example.

aryl is understood to be a phenyl radical which can be substituted by one or more fluorine atoms, or a pyridinyl radical which can be substituted by one or more fluorine atoms, or an imidazole radical.

α-aminoacyl is understood to be a radical of —C(=O) CH(Y)NH2 type, Y corresponding to the side chain of one of the proteinogenic amino acids, that is to say of the amino acids constituting the proteins.

α-amino acid is understood to be a radical of —NHCH(Y)COOH type, Y corresponding to the side chain of one of the proteinogenic amino acids, that is to say of the amino acids constituting the proteins.

oligomer is understood to be any compound consisting of the sequence of 2 to 15 monomers as described in the invention connected together by means of an ester type bond.

polymer is understood to be any compound consisting of the sequence of more than 15 monomers as described in the invention connected together by means of an ester type bond.

cyclic dimer is understood to be the compound consisting of the following formula:

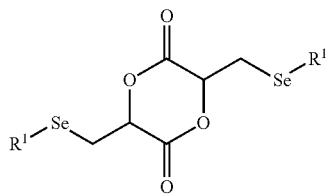

which connects together 2 monomers of compounds of general formula (I) as described in the invention by means of 2 ester bonds between the 2 hydroxy acid groups.

In another embodiment, the compound of formula (I) is selected from the compounds mentioned as examples.

Thus, the selenium compound of formula (I) can be selected from the group consisting of:
2-hydroxy-3-(methylseleno)propanoic acid methyl ester;
(R)-2-hydroxy-3-(methylseleno)propanoic acid methyl ester;
(S)-2-hydroxy-3-(methylseleno)propanoic acid methyl ester;
2-hydroxy-3-(methylseleno)propanoic acid ethyl ester;
2-hydroxy-3-(methylseleno)propanoic acid tert-butyl ester;
(S)-(2-hydroxy-3-(methylseleno)propanoic acid benzyl ester;
3-(ethylseleno)-2-hydroxypropanoic acid methyl ester;
2-hydroxy-3-(isobutylseleno)propanoic acid methyl ester;
2-hydroxy-3-(methylseleno)propanoic acid isopropyl ester;
2-hydroxy-3-(methylseleno)propanoic acid;
(R)-2-hydroxy-3-(methylseleno)propanoic acid;
(S)-2-hydroxy-3-(methylseleno)propanoic acid;
3-ethylseleno-2-hydroxypropanoic acid;
2-hydroxy-3-(isobutylseleno)propanoic acid;
dicyclohexylammonium 2-hydroxy-3-(methylseleno)propanoate salt;
sodium 2-hydroxy-3-(methylseleno)propanoate salt;
magnesium bis(2-hydroxy-3-(methylseleno)propanoate salt;
zinc bis(2-hydroxy-3-(methylseleno)propanoate salt;
calcium bis(2-hydroxy-3-(methylseleno)propanoate salt;
2-hydroxy-3-(methylseleno)propanamide;
N-cyclopropyl-2-hydroxy-3-(methylseleno)propanamide;
N-[2-(dimethylamino)ethyl]-2-hydroxy-3-(methylseleno) propanamide;
2-hydroxy-3-(methylseleno)-1-(pyrrolidin-1-yl)propan-1-one;
2-hydroxy-3-(methylseleno)-1-(piperidin-1-yl)propan-1-one;
2-hydroxy-3-(methylseleno)-1-(morpholin-4-yl)propan-1-one;
N,N-diethyl-2-hydroxy-3-(methylseleno)propanamide;
2-hydroxy-N-(2-hydroxyethyl)-3-(methylseleno)propanamide;
[(2RS)-2-hydroxy-3-methylselenopropanoyl]-(S)-alanine tert-butyl ester;
[(2RS)-2-hydroxy-3-methylselenopropanoyl]-(S)-alanine;
[(2RS)-2-hydroxy-3-methylselenopropanoyl]-(S)-methionine methyl ester;
[(2RS)-2-hydroxy-3-methylselenopropanoyl]-(S)-methionine;
[(2R)-2-hydroxy-3-methylselenopropanoyl]-(S)-methionine methyl ester;
[(2R)-2-hydroxy-3-methylselenopropanoyl]-(S)-methionine;
[(2S)-2-hydroxy-3-methylselenopropanoyl]-(S)-methionine methyl ester;
[(2 S)-2-hydroxy-3-methylselenopropanoyl]-(S)-methionine;
N(α)-[(2RS)-2-hydroxy-3-methylselenopropanoyl]-N(ω)-tert-butoxycarbonyl-(S)-lysine methyl ester;
N(α)-[(2RS)-2-hydroxy-3-methylselenopropanoyl]-N(ω)-fluorenylmethyloxycarbonyl-(S)-lysine methyl ester;
N(α)-[(2RS)-2-hydroxy-3-methylselenopropanoyl]-N(ω)-benzyloxycarbonyl-(S)-lysine methyl ester;
[(2RS)-2-hydroxy-3-methylselenopropanoyl]-(S)-selenomethionine methyl ester;

[(2RS)-2-hydroxy-3-methylselenopropanoyl]-(S)-selenomethionine;
[(2R)-2-hydroxy-3-methylselenopropanoyl]-(S)-selenomethionine methyl ester;
[(2R)-2-hydroxy-3-methylselenopropanoyl]-(S)-selenomethionine;
[(2S)-2-hydroxy-3-methylselenopropanoyl]-(S)-selenomethionine methyl ester;
[(2S)-2-hydroxy-3-methylselenopropanoyl]-(S)-selenomethionine;
2-(acetyloxy)-3-(methylseleno)propanoic acid;
2-(dodecanoyloxy)-3-(methylseleno)propanoic acid;
2-(benzoyloxy)-3-(methylseleno)propanoic acid methyl ester;
2-(benzoyloxy)-3-(methylseleno)propanoic acid;
3-(methylseleno)-2-[(3'-pyridine)oxycarbonyl]propanoic acid methyl ester;
2-[(tert-butoxycarbonyl)oxy]-3-(methylseleno)propanoic acid methyl ester;
2-[(tert-butoxycarbonyl)oxy]-3-(methylseleno)propanoic acid;
(2RS)—[N-(tert-butoxycarbonyl)-S-methionyl]-3-(methylseleno)propanoic acid methyl ester;
4-methylseleno-2-(2'-acetyloxy-3'-methylselenopropanoyl) butyric acid methyl ester;
4-methylseleno-2-(2'-acetyloxy-3'-methylselenopropanoyl) butyric acid;
3-methylseleno-2-(2'-acetoxy-4'-mnethylselenobutanoyl) propanoic acid methyl ester;
3-methylseleno-2-(2'-hydroxy-4'-methylseenobutanoyl)propanoic acid;
2-(pentanoyloxy)-3-(methylseleno)propanoic acid;
2-(nonanoyloxy)-3-(methylseleno)propanoic acid;
2-(linoleoyloxy)-3-(methylseleno)propanoic acid;
2-(linoleoyloxy)-3-(methylseleno)propanoic acid methyl ester;
2-(pivaloyloxy)-3-(methylseleno)propanoic acid;
2-(3-chloropropanoyloxy)-3-(methylseleno)propanoic acid;
2-{(1H-imidazoyl-4-ylcarbonyl)oxy)}-3-(methylseleno) propanoic acid;
2-(pivaloyloxy)-3-(methylseleno)propanoic acid methyl ester;
as well as the mixtures thereof in any proportions.

According to a second aspect, the invention relates to a method for preparing the novel organoselenium compounds and the ester and amide derivatives thereof of general formula (I), which is explained in FIG. 1, and which is characterized in that it includes the following steps:

1) reaction of a racemic (DL) oxirane-2-carboxylic acid ester or one of the enantiomers thereof (D or L) which are commercially available (for example, from SAF France), with
a/ either a dialkylaluminum alkylselenolate derivative of formula $Al(R^1)_2SeR^1$, which is itself generated in situ from the corresponding trialkyl aluminum $Al(R^1)_3$, which is commercially available (for example, from SAF, France), and elemental selenium Se(0) which is commercially available (for example, from SAF, France) (according to Kozikowski A P and Ames A, 1978, J. Org. Chem., 43(13):2735).
b/ or an alkylselenol $R^1SeH$, which is itself prepared in situ from an alkali metal salt of alkyl selenolate of formula $R^1$—Se-$M_1$ which is itself obtained by reduction of the corresponding dialkyl diselenide which is commercially available (for example, from SAF, France) or by reaction between metal selenium Se(0) and a corresponding alkyl lithium salt which is commercially available (for example, from SAF, France), where $M_1$ represents an alkali metal atom), which is reacted with ammonium chloride (by analogy with the opening of the alkyl oxirane carboxylates with a thiol as described in Org. Letters, 2004, 6(4), 497);

2) if applicable, one or more of the following reactions or series of reactions (see FIG. 1) which are well known to the person skilled in the art:
hydrolysis of the ester function, then
acidification of the reaction medium in order to obtain the corresponding acids of formula (I) where X=OH; then
esterification of the acids of formula (I) or of the alkali metal salts thereof of formula (Ia) with an alcohol or an alkyl halide in order to obtain the corresponding esters of general formula (I) where $X=OR^3$, with $R^3$ as defined above;
amidification of the acids of formula (I) with an appropriate amine of formula $R^4R^5NH$ or $NH_3$ where $R^5$ is as defined above, in order to obtain the compound of general formula (I) where X=NH2, $NR^4R^5$ or α-amino acid, $CH_3SeCH_2CH_2CH(COOH)NH$—;
esterification, when $R^2=H$, of the hydroxyl function by an appropriate acid in order to obtain the compound of general formula (I) where $OR^2$ is different from the OH group;
salification by an acid or by a base.

According to a particular implementation of the method according to the invention:
the selenium reagent is:
either a dialkylaluminum alkylselenolate, and for example dimethylaluminum methylselenolate generated in situ from metal selenium Se(0) and trimethyl aluminum $(Al(CH_3)_3$ in an aprotic solvent such as tetrahydrofuran (THF), for example.
or an alkylselenol, generated in situ from metal selenium Se(O) and alkyllithium, in an aprotic solvent such as tetrahydrofuran (THF), for example, and then put in the presence of ammonium chloride.

One operates in an aprotic polar solvent such as THF, for example. The subsequent reactions leading to the different compounds of formula (I), namely acidification, esterification, amidification, salification, are performed under conditions well known to the person skilled in the art.

The oligomers (dimers, trimers) and polymers, linear or branched, acyclic or cyclic, obtained between two or more molecules of derivatives of formula (I) described in the invention by esterification reaction between the alcohol and carboxylic acid functions present if applicable, considered alone or in a mixture, are obtained by condensation and dehydration by analogy with the examples described in Acta Chemica Scandinavica B, 1980, 34, 633-636 or else according to EP2238124.

In the context of the preparation of seleno-methyl esters (RCOSeMe), Kosikowski and Ames describe the obtention, in a minor proportion, of an undesired byproduct which is ethyl 3-methylseleno-2-hydroxypropanoate [Kosikowski, A P and Ames A, 1978, J. Org. Chem., 43(13):2735]. Although not part of the invention, this compound is structurally similar to the compounds of general formula (I) described in the present invention.

According to a third aspect, the invention also relates to the use of at least one selenium compound of general formula (I) as defined above, as pharmaceutical agent, in particular as antitumor agent, alone or combined with at least one other pharmaceutical agent and in particular with at least one antitumor agent.

Antitumor agent is understood to be any agent having the property of treating a tumor or "cancer" as it is commonly called.

According to a fourth aspect, the invention also relates to a pharmaceutical composition that includes at least one pharmaceutically active ingredient including at least one selenium compound of general formula (I) as defined above, alone or combined with at least one other pharmaceutically active ingredient.

In particular, the selenium compound of general formula (I) as defined above according to the invention makes it possible to carry out the treatment of tumors or cancers, either alone or in combination with one or more other known anticancer or cytotoxic agents, and either by pre-administration or by co-administration, such as tumors or cancers of the prostate, of the liver, of the kidneys, of the pancreas, of the lungs, of the colon and of the skin, in particular; Other anticancer agents are understood to be the following compounds: the matrix metalloproteinase inhibitors such as aminoglutethimide, estramustine, medroxyprogesterone acetate, leuprolide, flutamide, toremifene, Zoladex; the VEGF inhibitors, such as the anti-VEGF antibodies (Avastin (R)) and the small molecules such as ZD6474 and SU6668; vatalanib, BAY-43-9006, SU11248, CP-547632, and CEP-7055; the EGFR inhibitors, such as gefitinib, erlotinib, ABX-EGF, EMD72000, 11F8, and cetuximab; the Eg5 inhibitors, such as SB-715992, SB-743921, and MKI-833; the PAN inhibitors, such as canertinib, EKB-569, CI-1033, AEE-788, and XL-647; the kinase inhibitors, such as 2C4, GW-572016, Gleevec (R) and dasatinib (Sprycel (R); Casodex (R) (bicalutamide, Astra Zeneca), tamoxifen; the MAPK kinase inhibitors, the PI3 kinase inhibitors, the PDGF inhibitors, such as imatinib; the receptor tyrosine kinase inhibitors, the inhibitors of integrin signaling; tubulin; the acting agents such as vinblastine, vincristine, vinorelbine, vinflunine, paclitaxel, docetaxel, 7-O-methylthiomethylpaclitaxel, 4-deacetyl-4-methylcarbonatepaclitaxel, C-4 methyl carbonate paclitaxel, epothilone A, epothilone B, epothilone C, epothilone D, deoxyepothilone A, deoxyepothilone B, oxabicyclo[14.1.0]heptadecane-5-9-dione (ixabepilone), and derivatives thereof; the CDK inhibitors, the antiproliferative cell cycle inhibitors, epidophyllotoxin, etoposide, VM-26; the topoisomerase I or II inhibitors, such as camptothecin, topotecan, SN-38, procarbazine, mitoxantrone; the platinum coordination complexes such as cisplatin, carboplatin and oxaliplatin; the growth inhibitors, the antihormonal therapeutic agents; leucovorin; tegafur; the antemetabolites such as the purine antagonists (for example, 6-thioguanine and 6-mercaptopurine); the glutamine antagonists.

Other cytotoxic agents are understood to be the following compounds: cyclophosphamide, doxorubicin, daunorubicin, mitoxantrone, melphalan, hexamethyl melamine, thiotepa, cytarabine, idatrexate, trimetrexate, dacarbazine, L-asparaginase, bicalutamide, leuprolide, the pyridobenzoindole derivatives, the interferons, the interleukins.

According to a fifth aspect, the invention relates to the pharmaceutical compositions containing the selenium compounds of general formula (I) as active ingredient.

According to this fifth aspect of the present invention, the compounds of general formula (I) are used, for example, in quantities between 0.02% and 0.15% selenium equivalents (Se eq.) by weight of the preparation.

According to this fifth aspect of the present invention, the pharmaceutical compositions include a pharmaceutically acceptable carrier and a therapeutically effective quantity of one or more of the compounds of the present invention or of a stereoisomer, of a tautomer, of a pharmaceutically acceptable salt. These carriers can in particular consist of:

an injectable or potable solution,
a solid medium composed of one or more excipients which can be selected from vitamins, natural antioxidants such as L-ergothioneine, mineral salts, mono-, di- or polysaccharides, in particular folic acid, vitamins $B_6$, E or C, lactose, starch. This solid medium composed of one or more excipients as defined above, and including at least one of the compounds of general formula (I), can be formulated in the form of a capsule, a tablet or a powder.

According to this fifth aspect of the present invention, the pharmaceutical compositions containing at least one of the compounds of general formula (I) as active ingredient can be administered, depending on the case, by oral route, intravenous route, parenteral route, topical route including the transdermal route or nasal route or ocular route, or by inhalation. The quantities of the different constituents of these compositions, other than the compounds of general formula (I), are those usually used for the mentioned applications.

The present invention includes all combinations of the aspects and/or embodiments of the invention mentioned above. It is understood that any embodiment of the present invention can be considered in conjunction with another embodiment in order to describe additional more preferred embodiments. It is also well understood that each individual element of the preferred embodiments is its own independent preferred embodiment.

DESCRIPTION OF THE FIGURES

FIG. 1: Diagram of the process of synthesis of the compounds according to general formula (I)

FIG. 2: Viability percentage of cells DU145 and LS174T versus the concentration of compound 4, after 96 hours of treatment FIG. 3: Viability percentage of cells DU145, LS174T and HT-29 versus the concentration of compound 10, after 96 hours of treatment FIG. 4: Viability percentage of cells PC3, DU145, PANC-1 and MIA PaCa-2 versus the concentration of compound 38, after 96 hours of treatment FIG. 5: Viability percentage of cells HT-29, LS174T, HepG2 and MCF-7 versus the concentration of compound 38, after 96 hours of treatment

EXAMPLES

The following examples, as well as the diagram of the method according to the invention (FIG. 1) and the other figures, are provided only for the purpose of illustration and can in no way limit the scope of the invention.

In the examples described below, all the percentages are given in weight, the temperature is the ambient temperature or given in degree Celsius, and the pressure is atmospheric pressure unless otherwise indicated.

The used reagents are as commercially available from international suppliers such as SAF (France), Alfa Aesar, Fisher Scientific, TCI Europe, Bachem (Switzerland), except for the following compounds, which were prepared according to the protocol cited: oxirane-2-carboxylate ethyl ester (according to Org. Synth. 2006, 83, 162-169); oxirane-2-carboxylate tert-butyl ester (according to J. Am. Chem. Soc. 2008, 130 (31), 10096-10102), and (R)-oxirane-2-carboxylate benzyl ester (J. Org. Chem. 1992, 57 (11), 3380-3387).

I. Preparation Examples of the Compounds According to the Invention

1a—Preparations of Compounds a by the Introduction of Selenium: 3-(Alkylseleno)-2-Hydroxypropanoic Acid Esters The compounds A are prepared by reacting an alkylselenol $R^1SeH$ or a dialkylaluminum alkylselenolate $Al(R^1)_2SeR^1$ (generated in situ from trialkyl aluminum and elemental selenium Se(0) according to A. P. Kozikowski and A. Ames, J. Org. Chem. 1978, 43, 2735), with an alkyl oxirane carboxylate.

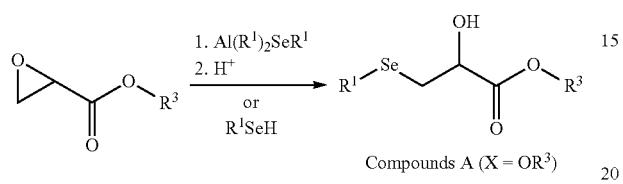

Compounds A (X = OR³)

Example A1

Preparation of the methyl ester of 2-hydroxy-3-(methylseleno)propanoic acid (Compound 1) using dimethylaluminum methylselenolate

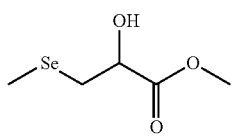

Compound 1

8.6 g (12.6 mL; 25.2 mmol; 1.1 equiv.) of a 2 M solution of trimethylaluminum in toluene are added dropwise (duration of addition 15 min) under nitrogen to 2.0 g (25.2 mmol; 1.1 equiv.) of selenium Se(0). The suspension is stirred for 15 min at ambient temperature, then for 2 h at reflux in a closed environment. The environment is allowed to return to ambient temperature and then cooled to 0° C. under nitrogen.

2.386 g (22.9 mmol) of methyl oxirane-2-carboxylate in solution in 12 mL of dichloromethane are added dropwise to the reaction medium (duration of addition 15 min). The medium is left under stirring for 30 min at 0° C. and then for 16 h at ambient temperature.

The reaction medium is cooled to −4° C. for 15 min. 1.286 g (24.05 mmol; 1.05 equiv.) of ammonium chloride in 10 mL of water are added very slowly dropwise to the reaction medium (duration of addition 15 min), because a very strong gaseous evolution occurs (Attention: generation and evolution of methane). 20 mL of dichloromethane are added dropwise, then the medium is stirred for 10 min without heating. 20 mL of a saturated $NH_4Cl$ aqueous solution are added dropwise, then the medium is stirred for 10 min without heating.

The reaction medium is filtered on Celite which is rinsed with dichloromethane (7×20 mL). The organic phase is decanted, and the aqueous phase is extracted with dichloromethane (3×20 mL). The organic phases are combined, dried with $Na_2SO_4$, filtered and concentrated.

The yellow oil obtained is distilled at a reduced pressure of 8 mbar (125° C.). The yield consists of 1.998 g (42%) of compound 1 in the form of a yellow oil.

$^1$H NMR ($CDCl_3$, 400 MHz): δ (ppm)=2.09 (s, 3H); 2.91 (m, 1H); 3.01 (m, 1H); 3.18 (m, 1H); 3.83 (s, 3H); 4.51 (m, 1H).

$^{13}$C NMR ($CDCl_3$, 75 MHz): δ (ppm)=5.9; 29.9; 53.1; 70.7; 174.1

UPLC-MS (AP+): 220.8 $(M+Na)^+$

Example A2

Preparation of the methyl ester of 2-hydroxy-3-(methylseleno)propanoic acid (Compound 1) using methylselenol

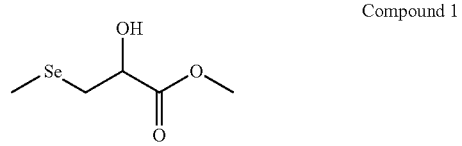

Compound 1

992 mg (12.5 mmol; 1 eq.) of selenium Se(0) are suspended under nitrogen in 44 mL of THF. The suspension is cooled to −3° C., then 6.2 mL (18.6 mmol; 1.49 eq.) of a 3 M methyllithium solution in diethoxymethane are added dropwise (addition time 7 min). The completely discolored medium is stirred for 20 min without heating, then 802 mg (15 mmol; 1.2 eq.) of ammonium chloride dissolved in 44 mL of methanol are added dropwise. The medium is stirred for 20 min without heating, then 2.11 mL (15 mmol; 1.2 eq.) of triethylamine are added. The medium is stirred for 20 min without heating, then 1.71 g (16.25 mmol; 1.3 eq.) of methyl oxirane-2-carboxylate are added. The medium is stirred for 1 h at 0° C., then for 22 h at ambient temperature.

The reaction medium is cooled to 0° C. for 15 min. 90 mL of dichloromethane are added dropwise, then the medium is stirred for 10 min without heating. 90 mL of a saturated $NH_4Cl$ aqueous solution are added dropwise, then the medium is stirred for 10 min without heating. The medium is diluted with 90 mL of water. The organic phase is recovered, and the aqueous phase is extracted with dichloromethane (2×90 mL). The organic phases are combined, dried with $Na_2SO_4$, filtered and concentrated. The yellow oil obtained is purified on a silica column (cyclohexane/ethyl acetate).

The yield consists of 330 mg (14%) of compound 1.

Example A3

Preparation of the methyl ester of (R)-2-hydroxy-3-(methylseleno)propanoic acid (Compound 2)

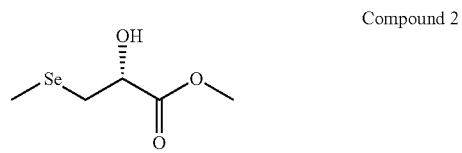

Compound 2

Compound 2 is obtained using the conditions of Example A1, starting with 4.959 g of methyl (S)-oxirane-2-carboxylate. After rinsing the Celite and evaporation of the solvents, the oil obtained is purified on a silica column (cyclohexane/ethyl acetate).

The yield consists of 3.257 g (33%) of compound 2 in the form of a yellow oil.

The $^1$H NMR spectrum is identical to the one obtained in Example A1.

[α]$_D$: −11.5 (c=1.0; MeOH)

Example A4

Preparation of the methyl ester of (S)-2-hydroxy-3-(methylseleno)propanoic acid (Compound 3)

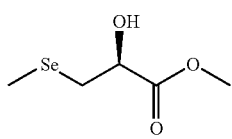

Compound 3

Compound 3 is obtained using the conditions of Example A1, starting with 7 g of methyl (R)-oxirane-2-carboxylate. After rinsing the Celite and evaporation of the solvents, the oil obtained is purified on a silica column (cyclohexane/ethyl acetate).

The yield consists of 4.04 g (29%) of compound 3 in the form of an orange oil.

The $^1$H NMR spectrum is identical to the one obtained in Example A1.

[α]$_D$: −11.1 (c=1.0; MeOH)

Example A5

Preparation of the ethyl ester of 2-hydroxy-3-(methylseleno)propanoic acid (Compound 4)

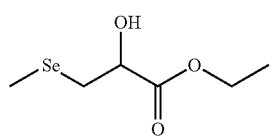

Compound 4

Compound 4 is obtained using the conditions of Example A1, starting with 1.56 g of ethyl oxirane-2-carboxylate. After rinsing the Celite and evaporation of the solvents, the oil obtained is purified on a silica column (cyclohexane/ethyl acetate).

The yield consists of 1.188 g (38%) of compound 4 in the form of a yellow oil.

$^1$H NMR (CDCl$_3$, 400 MHz): δ (ppm)=1.35 (t, J=7.0, Hz, 3H); 2.10 (s, 3H); 2.91 (dd, J=13.0, Hz, J=5.5 Hz, 1H); 3.01 (dd, J=13.0 Hz, J=4.0 Hz, 1H); 3.16 (d, J=6.0 Hz, 1H); 4.3 (q, J=7.0 Hz, 2H); 4.5 (td, J=5.5 Hz, J=4.0 Hz, 1H).

$^{13}$C NMR (CDCl$_3$, 75 MHz): δ (ppm)=6.0; 14.6; 29.9; 62.4; 70.8; 173.7

UPLC-MS (AP+): 234.8 (M+Na)$^+$

Example A6

Preparation of the tert-butyl ester of 2-hydroxy-3-(methylseleno)propanoic acid (Compound 5)

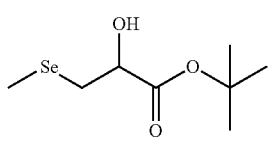

Compound 5

Compound 5 is obtained using the conditions of Example A1, starting with 1.0 g of tert-butyl oxirane-2-carboxylate. After rinsing the Celite and evaporation of the solvents, the oil obtained is purified on a silica column (cyclohexane/ethyl acetate).

The yield consists of 889 mg (54%) of compound 5 in the form of a slightly yellow oil.

$^1$H NMR (CDCl$_3$, 400 MHz): δ (ppm)=1.53 (s, 9H); 2.13 (s, 3H); 2.87 (dd, J=13.0 Hz, J=5.5 Hz, 1H); 2.97 (dd, J=13.0 Hz, J=4.0 Hz, 1H); 3.19 (d, J=5.5 Hz, 1H); 4.39 (td, J=5.5 Hz, J=4.0 Hz, 1H).

Example A7

Preparation of the benzyl ester of (S)-2-hydroxy-3-(methylseleno)propanoic acid (Compound 6)

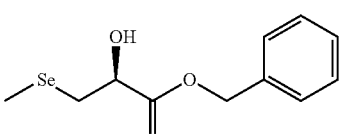

Compound 6

Compound 6 is obtained using the conditions of Example A1, starting with 622 mg of benzyl (R)-oxirane-2-carboxylate. After rinsing the Celite and evaporation of the solvents, the oil obtained is purified on a silica column (cyclohexane/ethyl acetate).

The yield consists of 325 mg (33%) of compound 6 in the form of a slightly yellowish oil.

$^1$H NMR (CDCl$_3$, 400 MHz): δ (ppm)=2.05 (s, 3H); 2.91 (dd, J=13.0 Hz, J=5.5 Hz, 1H); 3.02 (dd, J=13.0 Hz, J=4.5 Hz, 1H); 3.18 (d, J=5.5 Hz, 1H); 4.55 (td, J=5.5 Hz, J=4.5 Hz, 1H), 5.26 (s, 2H); 7.41 (m, 5H).

Example A8

Preparation of the methyl ester of 3-(ethylseleno)-2-hydroxypropanoic acid (Compound 7)

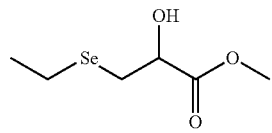

Compound 7

Compound 7 is obtained using the conditions of Example A1, starting with 2 g of selenium Se(0), 10.98 g of a 25% triethylaluminum solution in toluene and 2.386 g of methyl oxirane-2-carboxylate. After rinsing the Celite and evaporation of the solvents, the oil obtained is purified on a silica column (cyclohexane/ethyl acetate).

The yield consists of 1.977 g (40%) of compound 7 in the form of a yellow oil.

$^1$H NMR (CDCl$_3$, 400 MHz): δ (ppm)=1.41 (t, J=7.5 Hz, 3H); 2.67 (q, J=7.5 Hz, 2H); 2.92 (dd, J=13.0 Hz, J=5.5 Hz, 1H); 3.02 (dd, J=13.0 Hz, J=4.5 Hz, 1H); 3.18 (d, J=4.5 Hz, 1H); 3.82 (s, 3H), 4.5 (m, 1H).

$^{13}$C NMR (CDCl$_3$, 75 MHz): (ppm): 16.2; 18.9; 27.8; 53.1; 70.8; 174.1

Example A9

Preparation of the methyl ester of 2-hydroxy-3-(isobutylseleno)propanoic acid (Compound 8)

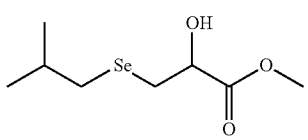

Compound 8

Compound 8 is obtained using the conditions of Example A1, starting with 2.0 g of selenium Se(0), 19.08 g of a 25% solution of triisobutyl aluminum in toluene and 2.386 g of methyl oxirane-2-carboxylate. After rinsing the Celite and evaporation of the solvents, the oil obtained is purified on a silica column (cyclohexane/ethyl acetate).

The yield consists of 2.291 g (42%) of compound 8 in the form of a yellow oil.

$^1$H NMR (CDCl$_3$, 300 MHz): δ (ppm)=0.77 (d, J=6.5 Hz, 6H); 1.61 (m, 11-1); 2.39 (d, J=7.0 Hz, 2H); 2.66 (dd, J=13.0 Hz, J=5.5 Hz, 1H); 2.76 (dd, J=13.0 Hz, J=4.5 Hz, 1H); 3.58 (s, 3H); 4.25 (m, 1H).

$^{13}$C NMR (CDCl$_3$, 75 MHz): (ppm)=22.9; 29.0; 29.7; 35.7; 53.1; 70.7; 174.0

1b—Preparation of the Compounds a by Esterification

The Compounds A can be obtained by introducing selenium reagents, as described in paragraph 1a above, but also by esterification of the Compounds B (for their preparation, see paragraph 2 below).

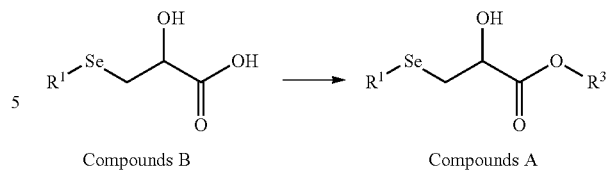

Compounds B → Compounds A

Example A10

Preparation of the ethyl ester of 2-hydroxy-3-(methylseleno)propanoic acid (Compound 4)

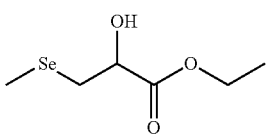

Compound 4

500 mg (2.68 mmol; 1 eq.) of 2-hydroxy-3-(methylseleno)propanoic acid (10, paragraph 2) are dissolved in 11 mL of absolute ethanol under nitrogen. 66 mg (1.07 mmol; 0.4 eq.) of orthoboric acid are added to the medium. The medium is left at reflux under stirring and under nitrogen for 48 h.

33 mg (535 µmol; 0.2 eq.) of orthoboric acid are added again to the medium.

The medium is left at reflux for 24 h.

The medium is concentrated to dryness, then the concentrate is redissolved with a semi-saturated NH4Cl aqueous solution (40 mL). The medium is extracted with ethyl acetate (3×40 mL). The organic phases are combined, dried with Na$_2$SO$_4$, filtered and concentrated.

The yield consists of 446 mg (77%) of compound 4 in the form of a yellow oil.

The $^1$H NMR spectrum is identical to the one obtained in Example A5.

Example A11

Preparation of the isopropyl ester of 2-hydroxy-3-(methylseleno)propanoic acid (Compound 9)

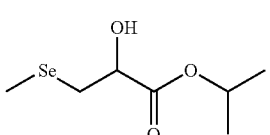

Compound 9

374 mg (2 mmol; 1 eq.) of 2-hydroxy-3-(methylseleno)propanoic acid (10) are dissolved in 8 mL of 2-propanol under nitrogen. 49 mg (800 µmol; 0.4 eq.) of orthoboric acid are added to the medium. The medium is left at reflux under stirring and under nitrogen for 48 h.

25 mg (400 µmol; 0.2 eq.) of orthoboric acid are added again to the medium.

The medium is left at reflux for 24 h.

The medium is concentrated to dryness, then the concentrate is redissolved with a semi-saturated NaHCO$_3$ aqueous solution (40 mL). The medium is extracted with ethyl acetate (3×40 mL). The organic phases are combined, dried with Na$_2$SO$_4$, filtered and concentrated. The oil obtained is purified on a silica column (cyclohexane/ethyl acetate).

The yield consists of 285 mg (62%) of compound 9 in the form of a yellow oil.

$^1$H NMR (CDCl$_3$, 400 MHz): δ (ppm)=1.32 (d, J=6.0 Hz, 6H); 2.11 (s, 3H); 2.89 (dd, J=13.0 Hz, J=5.5 Hz, 1H); 2.99 (m, 1H); 3.20 (s, 1H); 4.45 (m, 1H); 5.14 (m, 1H).

$^{13}$C NMR (CDCl$_3$, 75 MHz): δ (ppm)=6.0; 22.2; 29.8; 70.4; 70.9; 173.2

UPLC-MS (AP+): 248.9 (M+Na)$^+$

2—Preparation of the Compounds B and C: the 3-(alkylseleno)-2-hydroxypropanoic Acids and the Corresponding Salts The Compounds B are prepared by hydrolysis of the ester function of the Compounds A, and the corresponding salts C are obtained by reacting the compounds B with oxides or hydroxides:

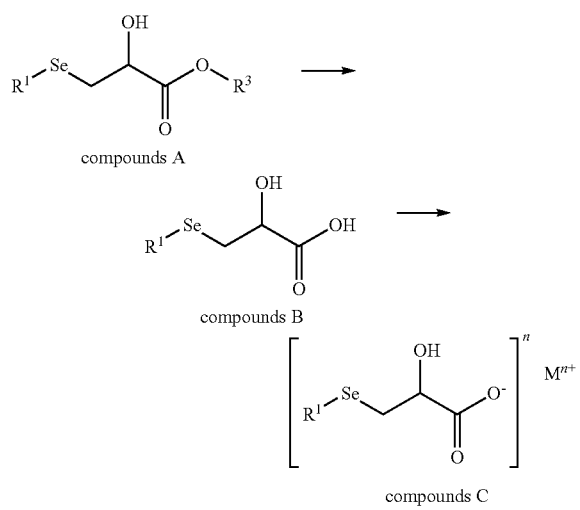

Example B1

Preparation of
2-hydroxy-3-(methylseleno)propanoic acid
(Compound 10) from the methyl ester

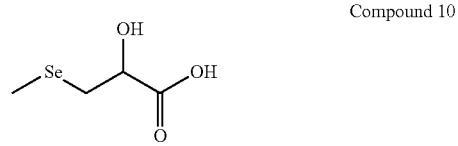

Compound 10

4.908 g (23.53 mmol) of compound 1 are dissolved in 14 mL of THF, 5 mL of methanol and 5 mL of demineralized water. 47.1 mL (47.07 mmol; 2 equiv.) of 1 M lithium hydroxide aqueous solution are added, the solution is stirred at ambient temperature for 16 h.

The pH of the medium is adjusted to 1 by adding a 2 M hydrochloric acid solution (14 mL). The medium is extracted with ethyl acetate (4×100 mL). The organic phases are combined, dried over Na$_2$SO$_4$, filtered and concentrated.

The yield consists of 4.177 g (95%) of compound 10 in the form of a pale yellow solid.

$^1$H NMR (D$_2$O, 400 MHz): δ (ppm)=2.08 (s, 3H); 2.92 (dd, J=13.5 Hz, J=6.5 Hz, 1H); 3.03 (dd, J=13.5 Hz, J=4.5 Hz, 1H); 4.57 (dd, J=6.5 Hz, J=4.5 Hz, 1H).

$^1$H NMR (DMSO, 400 MHz): δ (ppm)=1.99 (s, 3H); 2.70 (dd, J=12.5 Hz, J=6.5 Hz, 1H); 2.79 (dd, J=12.5 Hz, J=5.0 Hz, 1H); 4.18 (dd, J=6.5 Hz, J=5.0 Hz, 1H).

$^{13}$C NMR (CDCl$_3$, 75 MHz): δ (ppm)=6.0; 29.6; 70.1; 178.0

UPLC-MS (AP−): 182.6 (M−H$^+$)

Elemental analysis: C$_4$H$_8$O$_3$Se; Theoretical: C (26.24%); H (4.4%); Experimental: C (26.9%); H (4.42%)

Example B2

Preparation of
2-hydroxy-3-(methylseleno)propanoic acid
(Compound 10) from the tert-butyl ester The compound 10 is obtained using the conditions of Example B1, starting with 100 mg of tert-butyl 2-hydroxy-3-(methylseleno)propanoate (5).

The yield consists of 64 mg (82%) of the desired product in the form of a solid.

The $^1$H NMR spectrum is identical to the one obtained in Example B1.

Example B3

Preparation of
(R)-2-hydroxy-3-(methylseleno)propanoic acid
(Compound 11)

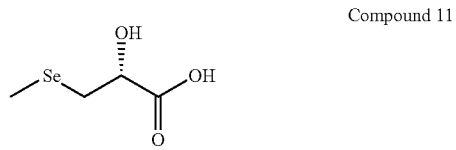

Compound 11

Compound 11 is obtained using the conditions of Example B1, starting with 2.117 g of methyl (R)-2-hydroxy-3-(methylseleno)propanoate (2).

The yield consists of 1.875 g (96%) of the desired product in the form of a yellow solid.

The $^1$H NMR spectrum is identical to the one obtained in Example B1.

[α]$_D$=+1.07 (c=6.0; EtOH)

Example B4

Preparation of
(S)-2-hydroxy-3-(methylseleno)propanoic acid
(Compound 12) from the methyl ester

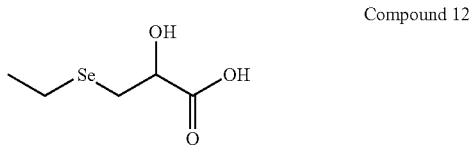

Compound 12

Compound 12 is obtained using the conditions of Example B1, starting with 2.95 g of methyl (S)-2-hydroxy-3-(methylseleno)propanoate (3).

The yield consists of 2.61 g (95%) of the desired product in the form of a yellow solid.

The $^1$H NMR spectrum is identical to the one obtained in Example B1.

$[\alpha]_D = -1.03$ (c=6.0; EtOH)

Example B5

Preparation of (S)-2-hydroxy-3-(methylseleno)propanoic acid (Compound 12) from benzyl ester

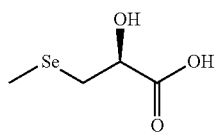

Compound 12

Compound 12 is obtained using the conditions of Example B1, starting with 494 mg of benzyl (S)-2-hydroxy-3-(methylseleno)propanoate (6).

After 16 h of stirring at ambient temperature, the reaction medium is extracted with ethyl acetate (2×30 mL). The pH of the medium is adjusted to 1 by adding 2 M hydrochloric acid aqueous solution. The medium is extracted with ethyl acetate (2×30 mL). The organic phases of this second extraction are combined, dried over $Na_2SO_4$, filtered and concentrated.

The yield consists of 280 mg (84%) of compound 12 in the form of a pale yellow solid.

The $^1$H NMR spectrum is identical to the one obtained in Example B1.

Example B6

Preparation of 3-ethylseleno-2-hydroxypropanoic acid (Compound 13) from the methyl ester

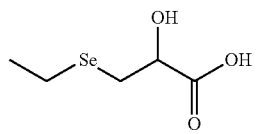

Compound 13

Compound 13 is obtained using the conditions of Example B1, starting with 500 mg of 3-(ethylseleno)-2-hydroxypropanoic acid methyl ester (7). The yield consists of 471 mg (100%) of compound 13 in the form of a pale yellow solid.

$^1$H NMR (CDCl$_3$, 400 MHz): δ (ppm)=1.44 (t, J=7.5 Hz, 3H); 2.71 (q, J=7.5 Hz, 2H); 3.00 (dd, J=13.5 Hz, J=6.0 Hz, 1H); 3.11 (dd, J=13.5 Hz, J=4.5 Hz, 1H); 4.55 (dd, J=6.0 Hz, J=4.5 Hz, 1H).

$^{13}$C NMR (CDCl$_3$, 75 MHz): (ppm)=16.1; 19.1; 27.6; 70.3; 177.9

UPLC-MS (AP-): 197.2 (M-H$^+$)

Example B7

Preparation of 2-hydroxy-3-(isobutylseleno)propanoic acid (Compound 14) from the methyl ester

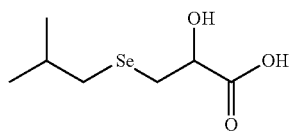

Compound 14

Compound 14 is obtained using the conditions of Example B1 starting with 500 mg of 2-hydroxy-3-(isobutylseleno)propanoic acid methyl ester (8).

The yield consists of 423 mg (90%) of compound 14 in the form of a pale yellow solid.

$^1$H NMR (CDCl$_3$, 400 MHz): δ (ppm)=1.03 (d, J=6.5 Hz, 6H); 1.88 (m, 1H); 1.95 (dd, J=7.0 Hz, 2H); 2.97 (dd, J=13.0 Hz, J=6.0 Hz, 1H); 3.08 (dd, J=13.0 Hz, J=4.5 Hz, 1H); 4.53 (m, 1H).

$^{13}$C NMR (CDCl$_3$, 75 MHz): (ppm)=22.9; 28.7; 29.7; 35.8; 70.2; 177.9

UPLC-MS (AP-): 225.3 (M-H$^+$)

Example C1

Preparation of the dicyclohexylammonium 2-hydroxy-3-(methylseleno)propanoate salt (Compound 15)

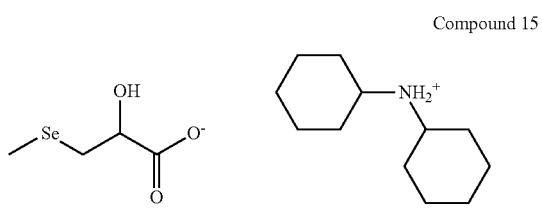

Compound 15

373 mg (2 mmol) of 2-hydroxy-3-(methylseleno)propanoic acid are dissolved in 2 mL of acetone. 733 mg (805 μL; 4 mmol; 2 eq.) of dicyclohexylamine are added to the medium.

A precipitate appeared instantaneously and is filtered, rinsed with acetone (2×10 mL), then with a 1/1 ethyl acetate/cyclohexane mixture (2×10 mL).

The yield consists of 524 mg (70%) of compound 15 in the form of a white solid.

$^1$H NMR (CDCl$_3$, 400 MHz): δ (ppm)=1.26 (m, 7H); 1.50 (m, 4H); 1.68 (m, 2H); 1.84 (m, 4H); 2.06 (m, 4H); 2.12 (s, 3H); 2.91 (dd, J=12.5 Hz, J=6. Hz, 1H); 3.02 (m, 3H); 4.22 (m, 1H).

$^{13}$C NMR (CDCl$_3$, 75 MHz): δ (ppm)=5.7; 25.2; 25.5; 29.4; 31.6; 53.2; 72.2; 177.7

Example C2

Preparation of sodium 2-hydroxy-3-(methylseleno)propanoate salt (Compound 16)

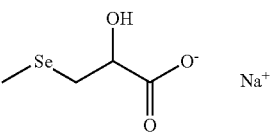

Compound 16

80 mg (2 mmol) of 60% sodium hydroxide in mineral oil are suspended under nitrogen in 2 mL of THF. 373 mg (2 mmol) of 2-hydroxy-3-(methylseleno)propanoic acid dissolved in 2 mL of THF are added dropwise in 5 min.

The medium is cooled in a water-ice bath, then cyclohexane (3 mL) is added.

A precipitate forms. The medium is filtered, then the solid is washed with cyclohexane (3 mL), then with TBME (3×3 mL).

The yield consists of 315 mg (75%) of compound 16 in the form of an off-white solid.

$^1$H NMR (D$_2$O, 400 MHz): δ (ppm)=2.08 (s, 3H); 2.88 (dd, J=13.0 Hz, J=6.5 Hz, 1H); 2.99 (dd, J=13.0 Hz, J=4.0 Hz, 1H); 4.32 (dd, J=6.5 Hz, J=4.0 Hz, 1H).

$^{13}$C NMR (D$_2$O, 75 MHz): δ (ppm)=4.8; 30.0; 71.7; 179.4

UPLC-MS (AP−): 182.7 (M−Na$^+$)

Example C3

Preparation of the magnesium bis(2-hydroxy-3-(methylseleno)propanoate salt (Compound 17)

Compound 17

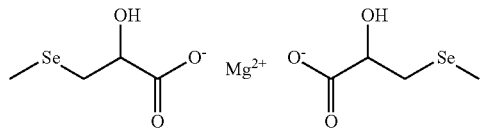

495 mg (2.65 mmol) of 2-hydroxy-3-(methylseleno)propanoic acid are dissolved in 1 mL of demineralized water, then 50 mg (1.25 mmol) of magnesium oxide are added. The medium is stirred at ambient temperature for 16 h.

The medium is diluted with acetone (2 mL), then the medium is filtered through fritted glass. The solid is rinsed with water (0.5 mL), then with TBME (2 mL). The solid is dried under a vacuum.

The yield consists of 565 mg of compound 17 in the form of a white solid (quantitative).

$^1$H NMR (D$_2$O, 400 MHz): δ (ppm)=2.04 (s, 3H); 2.83 (dd, J=13.0 Hz, J=6.5 Hz, 1H); 2.95 (dd, J=13.0 Hz, J=4.0 Hz, 1H); 4.25 (dd, J=6.5 Hz, J=4.0 Hz, 1H).

Example C4

Preparation of the zinc bis(2-hydroxy-3-(methylseleno)propanoate salt (Compound 18)

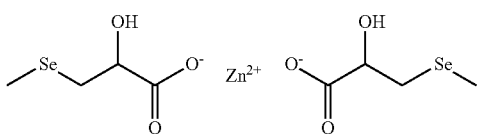

Compound 18

500 mg (2.65 mmol) of 2-hydroxy-3-(methylseleno)propanoic acid are dissolved in 1 mL of demineralized water, then 145 mg of basic zinc carbonate are added. 1 mL of demineralized water is added, then the medium is stirred at ambient temperature for 16 h.

The medium is diluted with acetone (2 mL), then the medium is filtered through fritted glass. The solid is rinsed with water (1 mL), then with acetone (3×2 mL). The solid is dried under a vacuum.

The yield consists of 496 mg (79%) of compound 18 in the form of a white solid.

$^1$H NMR (D$_2$O, 400 MHz): δ (ppm)=2.05 (s, 3H); 2.87 (dd, J=13.0 Hz, J=6.5 Hz, 1H); 2.98 (dd, J=13.0 Hz, J=4.0 Hz, 1H); 4.32 (dd, J=6.5 Hz, J=4.0 Hz, 1H).

Example C5

Preparation of the calcium bis(2-hydroxy-3-(methylseleno)propanoate salt (Compound 19)

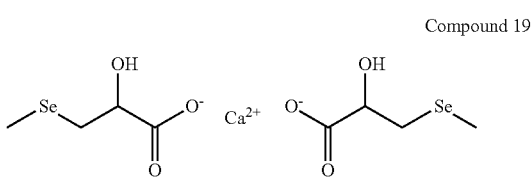

Compound 19

374 mg (2 mmol) of 2-hydroxy-3-(methylseleno)propanoic acid are dissolved in 0.9 mL of demineralized water, then 70 mg (945 μmol) of calcium hydroxide are added. 1.1 mL of demineralized water are added, then the medium is stirred at ambient temperature for 16 h.

The medium is filtered through fritted glass. The solid is rinsed with water (2×2 mL), then with tert-butyl methyl ether (TBME) (2×2 mL). The solid is dried under a vacuum. The yield consists of 74 mg (19%) of the desired product in the form of an off-white solid.

The filtrate is concentrated to dryness. The residue is triturated with TBME (5 mL). The solid is dried under a vacuum.

The yield consists of 205 mg (53%) of compound 19 in the form of an off-white solid.

$^1$H NMR (D$_2$O, 400 MHz): δ (ppm)=2.07 (s, 3H); 2.88 (dd, J=13.0 Hz, J=6.5 Hz, 1H); 2.99 (dd, J=13.0 Hz, J=4.0 Hz, 1H); 4.30 (dd, J=6.5 Hz, J=4.0 Hz, 1H).

$^{13}$C NMR (D$_2$O, 300 MHz): δ (ppm)=4.8; 30.4; 72.1; 180.1

3—Preparation of Compounds D: Amides Derived from 2-hydroxy-3-(alkylseleno)propanoic acid The Compounds D are prepared either by aminolysis of compounds A, or they are synthesized from compounds B by peptide coupling.

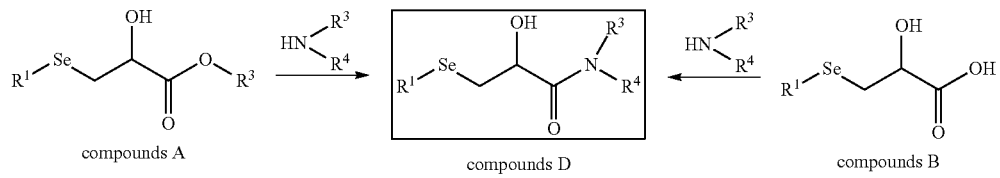

compounds A     compounds D     compounds B

Example D1

Preparation of 2-hydroxy-3-(methylseleno)propanamide (Compound 20)

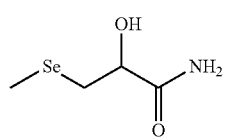

Compound 20

295 mg (1.5 mmol) of compound 1 are dissolved in 4.04 g (5.25 mL; 36.76 mmol; 24 equiv.) of a 20% aqueous ammonia solution. The medium is stirred at ambient temperature for 22 h.

The medium is evaporated to dryness then coevaporated with ethyl acetate.

The yield consists of 284 mg (100%) of compound 20 in the form of an off-white solid.

$^1$H NMR (MeOD, 400 MHz): δ (ppm): 2.11 (s, 3H); 2.85 (dd, J=13.0 Hz, J=7.0 Hz, 1H); 2.98 (dd, J=13.0 Hz, J=4.0 Hz, 1H); 4.3 (dd, J=7.0 Hz, J=4.0 Hz, 1H).

$^1$H NMR (DMSO, 400 MHz): δ (ppm)=1.97 (s, 3H); 2.68 (dd, J=12.5 Hz, J=7.0 Hz, 1H); 2.80 (dd, J=12.5 Hz, J=4.0 Hz, 1H); 4.04 (m, 1H); 5.58 (d, J=5.5 Hz, 1H); 7.19 (d, J=15.5 Hz, 2H)

$^{13}$C NMR (MeOD, 75 MHz): δ (ppm): 5.2; 31.0; 73.3; 179.2

UPLC-MS (AP+): 183.8 (M+H)$^+$
UPLC-MS (AP+): 206.0 (M+Na)$^+$

Example D2

Preparation of N-cyclopropyl-2-hydroxy-3-(methylseleno)propanamide (Compound 21)

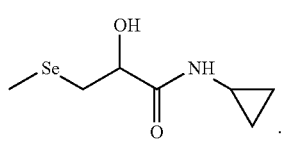

Compound 21

513 mg (2.5 mmol) of compound 1 are dissolved in 428 mg (519 μL; 7.5 mmol; 3 equiv.) of cyclopropylamine. The medium is stirred at 85° C. for 72 h.

The medium is allowed to return to ambient temperature, evaporated to dryness, then purified on a silica column (dichloromethane/methanol).

The yield consists of 452 mg (79%) of compound 21 in the form of a pale yellow solid.

$^1$H NMR (CDCl$_3$, 400 MHz): δ (ppm)=0.56 (m, 2H); 0.82 (m, 2H); 2.03 (s, 3H); 2.76 (m, 1H); 2.89 (dd, J=13.0 Hz, J=7.5 Hz, 1H); 3.08 (dd, J=13.0 Hz, J=4.5 Hz, 1H); 3.52 (d, J=3.5 Hz, 1H); 4.17 (m, 1H); 6.88 (s, 1H).

$^{13}$C NMR (CDCl$_3$, 75 MHz): δ (ppm)=4.9; 6.8; 6.9; 22.7; 31.6; 69.9; 173.8

UPLC-MS (AP+): 245.9 (M+Na)$^+$

Example D3

Preparation of N-[2-(dimethylamino)ethyl]-2-hydroxy-3-(methylseleno)propanamide (Compound 22)

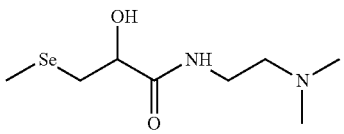

Compound 22

417 mg (2 mmol) of compound 1 are dissolved in 539 mg (674 μL; 6 mmol; 3 equiv.) of N,N-dimethylethylenediamine. The medium is stirred at 85° C. for 72 h.

The medium is allowed to return to ambient temperature, evaporated to dryness then purified on a silica column (dichloromethane/methanol).

The yield consists of 460 mg (89%) of compound 22 in the form of an orange oil.

$^1$H NMR (CDCl$_3$, 400 MHz): δ (ppm)=2.05 (s, 3H); 2.28 (s, 6H); 2.48 (t, J=6.0 Hz, 2H); 2.91 (dd, J=13.0 Hz, J=7.0 Hz, 1H); 3.06 (dd, J=13.0 Hz, J=4.0 Hz, 1H); 3.40 (m, 2H); 4.26 (dd, J=7.0 Hz, J=4.0 Hz, 1H); 7.34 (m, 1H).

$^{13}$C NMR (CDCl$_3$, 75 MHz): δ (ppm)=5.2; 31.6; 36.7; 45.6; 58.6; 71.0; 172.9

UPLC-MS (AP+): 254.9 (M+H)$^+$

Example D4

Preparation of 2-hydroxy-3-(methylseleno)-1-(pyrrolidin-1-yl)propan-1-one (Compound 23)

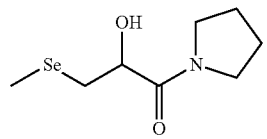

Compound 23

513 mg (2.5 mmol) of compound 1 are dissolved in 533 mg (616 μL; 7.5 mmol; 3 equiv.) of pyrrolidine. The medium is stirred at 85° C. for 48 h.

The medium is allowed to return to ambient temperature, evaporated to dryness, then purified on a silica column (cyclohexane/ethyl acetate).

The yield consists of 402 mg (66%) of compound 23 in the form of an orange oil.

$^1$H NMR (CDCl$_3$, 400 MHz): δ (ppm)=1.85-2.07 (m, 4H); 2.11 (s, 3H); 2.77 (dd, J=13.0 Hz, J=7.0 Hz, 1H); 2.85 (dd, J=13.0 Hz, J=4.5 Hz, 1H); 3.45-3.65 (m, 4H); 3.78 (d, J=8.0 Hz, 1H); 4.45 (m, 1H).

$^{13}$C NMR (CDCl$_3$, 75 MHz): δ (ppm)=5.8; 24.3; 26.5; 29.7; 46.7; 46.8; 70.2; 171.6

UPLC-MS (AP+): 237.9 (M+H)$^+$
UPLC-MS (AP+): 259.9 (M+Na)$^+$

Example D5

Preparation of 2-hydroxy-3-(methylseleno)-1-(piperidin-1-yl)propan-1-one (Compound 24)

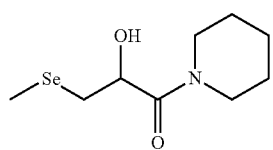

Compound 24

417 mg (2 mmol) of compound 1 are dissolved in 517 mg (600 μL; 6 mmol; 3 equiv.) of piperidine. The medium is stirred at 85° C. for 72 h.

The medium is allowed to return to ambient temperature, evaporated to dryness, then purified on a silica column (dichloromethane/acetone).

The yield consists of 151 mg (29%) of compound 24 in the form of a yellow oil.

$^1$H NMR (CDCl$_3$, 400 MHz): δ (ppm)=1.56-1.74 (m, 6H); 2.13 (s, 3H); 2.72 (dd, J=13.0 Hz, J=7.0 Hz, 1H); 2.82 (dd, J=13.0 Hz, J=4.0 Hz, 1H); 3.40 (d, J=4.0 Hz, 2H); 3.62 (m, 2H); 4.03 (d, J=7.0 Hz, 1H); 4.61 (m, 1H).

$^{13}$C NMR (CDCl$_3$, 75 MHz): δ (ppm)=6.0; 24.8; 25.8; 26.6; 30.4; 44.2; 46.5; 68.7; 171.3

UPLC-MS (AP+): 251.9 (M+H)$^+$
UPLC-MS (AP+): 273.9 (M+Na)$^+$

Example D6

Preparation of 2-hydroxy-3-(methylseleno)-1-(morpholin-4-yl)propan-1-one (Compound 25)

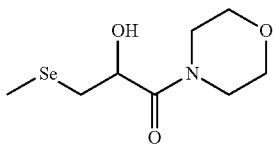

Compound 25

486 mg (2.4 mmol) of compound 1 are dissolved in 641 μL (7.2 mmol; 3 equiv.) of morpholine. The medium is stirred at 85° C. for 72 h.

The medium is allowed to return to ambient temperature, evaporated to dryness, then purified on a silica column (dichloromethane/acetone).

The yield consists of 262 mg (42%) of compound 25 in the form of a pale yellow oil.

$^1$H NMR (CDCl$_3$, 400 MHz): δ (ppm)=2.12 (s, 3H); 2.79 (m, 2H); 3.52 (m, 2H); 3.65 (m, 1H); 3.74 (m, 5H); 3.82 (d, J=8.0 Hz, 1H); 4.59 (m, 1H).

$^{13}$C NMR (CDCl$_3$, 75 MHz): δ (ppm)=6.1; 30.1; 43.3; 46.2; 66.8; 67.1; 68.6; 171.8

UPLC-MS (AP+): 253.9 (M+H)$^+$
UPLC-MS (AP+): 276.0 (M+Na)$^+$

Example D7

Preparation of N,N-diethyl-2-hydroxy-3-(methyl seleno)propanamide (Compound 26)

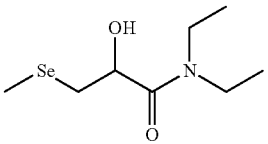

Compound 26

417 mg (2 mmol) of compound 1 are dissolved in 443 mg (633 μL; 6 mmol; 3 equiv.) of diethylamine. The medium is stirred at 85° C. for 72 h.

The medium is allowed to return to ambient temperature, evaporated to dryness, then purified on a silica column (dichloromethane/methanol).

The yield consists of 105 mg (19%) of compound 26 in the form of an orange oil.

$^1$H NMR (CDCl$_3$, 400 MHz): δ (ppm)=1.38 (t, J=7.0 Hz, 6H); 2.10 (s, 3H); 2.91 (dd, J=12.5 Hz, J=6.0 Hz, 1H); 3.02 (m, 5H); 4.33 (m, 1H).

Example D8

Preparation of 2-hydroxy-N-(2-hydroxyethyl)-3-(methylseleno)propanamide (Compound 27)

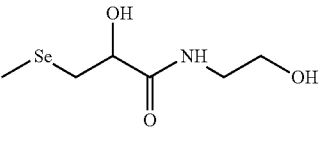

Compound 27

250 mg (1.22 mmol) of compound 1 are dissolved in 228 mg (225 μL; 3.66 mmol, 3 equiv.) of ethanolamine. The medium is stirred at 85° C. for 72 h.

The medium is allowed to return to ambient temperature, evaporated to dryness, then purified on a silica column (dichloromethane/methanol).

The yield consists of 203 mg (72%) of compound 27 in the form of a greenish oil.

$^1$H NMR (CDCl$_3$, 400 MHz): δ (ppm)=2.06 (s, 3H); 2.92 (dd, J=13.0 Hz, J=7.5 Hz, 1H); 2.95 (s, 1H); 3.11 (dd, J=13.0 Hz, J=4.0 Hz, 1H); 3.49 (m, 2H); 3.65 (d, J=4.5 Hz, 1H); 3.78 (m, 2H); 4.26 (m, 1H); 7.26 (s, 1H).

$^{13}$C NMR (CDCl$_3$, 75 MHz): δ (ppm)=5.2; 31.2; 42.5; 62.2; 70.6; 173.9

UPLC-MS (AP+): 227.9 (M+H)$^+$
UPLC-MS (AP+): 249.8 (M+Na)$^+$

Example D9

Preparation of [(2RS)-2-hydroxy-3-methylseleno-propanoyl]-(S)-alanine (Compound 29)

D9.1. Preparation of the tert-butyl ester of [(2RS)-2-hydroxy-3-methylselenopropanoyl]-(S)-alanine (Compound 28)

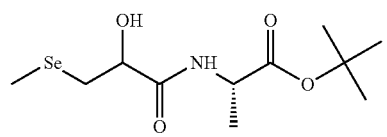

Compound 28

100 mg (546 µmol) of 2-hydroxy-3-(methylseleno)propanoic acid (10) are dissolved under nitrogen in 5 mL of dichloromethane. The medium is cooled to 0° C., then 183 mg (600 µmol, 1.1 eq.) of 3-(diethoxyphosphoryloxy)-1,2,3-benzotriazin-4(3H)-one are added. The medium is stirred for 30 min at 0° C., then for 1 h 30 at ambient temperature. The medium is cooled to 0° C., then 99 mg (546 µmol, 1 eq.) of the hydrochloride of the tert-butyl ester of (S)-alanine and 156 mg (200 µL; 1.20 mmol; 2.2 eq.) of N,N-diisopropyl-ethylamine are added. The medium is stirred for 30 min at 0° C., then for 16 h at ambient temperature.

The reaction medium is diluted with dichloromethane (25 mL), then the medium is washed with a 1N hydrochloric acid aqueous solution (2×10 mL), then with an aqueous solution of NaHCO$_3$ (1N, 2×10 mL), then with a saturated NaCl aqueous solution (10 mL). The organic phase is dried over Na$_2$SO$_4$, filtered and concentrated. The residue is purified on a silica column (cyclohexane/ethyl acetate).

The yield consists of 116 mg (67%) of compound 28 in the form of a colorless oil.

$^1$H NMR (CDCl$_3$, 400 MHz) 50/50 mixture of 2 diastereoisomers 28a (R,S) and 28b (S,S): δ (ppm)=1.42 and 1.43 (2d, J=3.5 Hz, 3H); 1.49 and 1.50 (2s, 9H); 2.04 and 2.05 (2s, 3H); 2.92 (dd, J=13.0 Hz, J=7.5 Hz, 1H); 3.09 (m, 1H); 3.43 (d, J=3.5 Hz, 1H); 4.21 (m, 1H); 4.48 (m, 1H); 7.27 and 7.33 (2d, J=6.5 Hz, 1H).

UPLC-MS (AP−): 309.8 (M−H+)
UPLC-MS (AP+): 333.9 (M+Na)$^+$

D9.2: Preparation of [(2RS)-2-hydroxy-3-methyl-selenopropanoyl]-(S)-alanine (Compound 29)

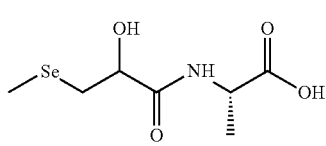

Compound 29

Compound 29 is obtained using the conditions of Example B1, starting with 58 mg of the ester 28.

The yield consists of 40 mg (81%) of compound 29 in the form of a colorless oil.

$^1$H NMR (CDCl$_3$, 400 MHz) 50/50 mixture of 2 diastereoisomers 29a (R,S) and 29b (S,S): δ (ppm)=1.51 and 1.53 (2d, J=3.0 Hz, 3H); 2.05 and 2.06 (2s, 3H); 2.90 (m, 1H); 3.10 (m, 1H); 3.52 (s, 1H); 4.24 and 4.31 (2dd, J=8.0 Hz, J=4.0 Hz, 1H); 4.61 (m, 1H); 7.36 and 7.43 (2d, J=7.5 Hz, 1H).

Example D10

Preparation of [(2RS)-2-hydroxy-3-methylseleno-propanoyl]-(S)-methionine (Compound 31)

D10.1. Preparation of the methyl ester of [(2RS)-2-hydroxy-3-methylselenopropanoyl]-(S)-methionine (Compound 30)

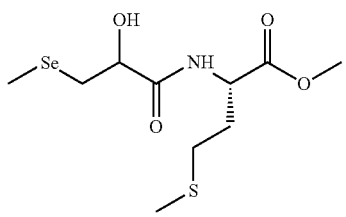

Compound 30

Compound 30 is obtained using the conditions of Example D9, starting with 500 mg (2.65 mmol; 1 eq.) of 2-hydroxy-3-(methylseleno)propanoic acid (10) and 557 mg (2.65 mmol; 1 eq.) of the methyl ester of the hydrochloride of (S)-methionine. The yield consists of 549 mg (60%) of the desired product in the form of a slightly yellow oil.

$^1$H NMR (CDCl$_3$, 400 MHz) 50/50 mixture of 2 diastereoisomers 30a (R,S) and 30b (S,S): δ (ppm)=2.05 (m, 4H); 2.13 (m, 3H); 2.23 (m, 1H); 2.56 (t, J=7.5 Hz, 2H); 2.92 (m, 1H); 3.09 (m, 1H); 3.45 (m, 1H); 3.79 and 3.80 (2s, 3H); 4.25 (m, 1H); 4.75 (m, 1H); 7.39 (m, 1H).

D10.2: Preparation of [(2RS)-2-hydroxy-3-methyl-selenopropanoyl]-(S)-methionine (Compound 31)

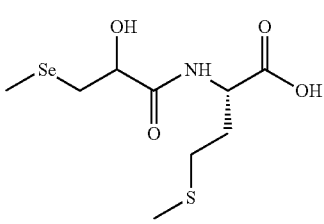

Compound 31

Compound 31 is obtained using the conditions of Example B1, starting with 445 mg of compound 30.

After 16 h of stirring at ambient temperature, the reaction medium is diluted in water (40 mL), then extracted with ethyl acetate (2×25 mL). The pH of the medium is adjusted to 1 by adding a 2 M hydrochloric acid aqueous solution. The medium is extracted with ethyl acetate (4×25 ml). The organic phases of this second extraction are combined, dried over Na$_2$SO$_4$, filtered and concentrated.

The yield consists of 400 mg (92%) of the desired product in the form of a pale yellow oil.

¹H NMR (CDCl₃, 400 MHz) 50/50 mixture of 2 diastereoisomers 31a (R,S) and 31b (S,S): δ (ppm)=2.05 and 2.08 (2s, 3H); 2.11 (m, 1H); 2.15 (s, 3H); 2.27 (m, 1H); 2.62 (t, J=7.5 Hz, 2H); 2.91 (m, 1H); 3.10 (m, 1H); 4.28 and 4.38 (2dd, J=8.0 Hz, J=4.5 Hz, 1H); 4.75 (m, 1H); 7.51 and 7.57 (2d, J=8.0 Hz, 1H).

Example D11

Preparation of [(2R)-2-hydroxy-3-methylselenopropanoyl]-(S)-methionine (Compound 31a)

D11.1 Preparation of the methyl ester of [(2R)-2-hydroxy-3-methylselenopropanoyl]-(S)-methionine (Compound 30a)

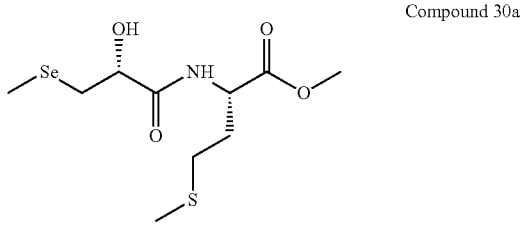

Compound 30a

Compound 30a is obtained using the conditions of Example D9, starting with 100 mg (513 μmol; 1 eq.) of (R)-2-hydroxy-3-(methylseleno)propanoic acid (11) and 108 mg (513 μmol; 1 eq.) of the methyl ester of the hydrochloride of (S)-methionine. The yield consists of 89 mg (50%) of the desired product in the form of a colorless oil.

¹H NMR (CDCl₃, 400 MHz): δ (ppm)=2.06 (s, 3H); 2.07 (m, 1H); 2.13 (s, 3H); 2.22 (m, 1H); 2.57 (t, J=7.5 Hz, 2H); 2.93 (dd, J=13.0 Hz, J=7.5 Hz, 1H); 3.09 (dd, J=13.0 Hz, J=4.5 Hz, 1H); 3.40 (d, J=4.0 Hz, 1H); 3.80 (s, 3H); 4.28 (m, 1H); 4.75 (m, 1H); 7.40 (d, J=8.0 Hz, 1H).

D11.2. Preparation of [(2R)-2-hydroxy-3-methylselenopropanoyl]-(S)-methionine (Compound 31a)

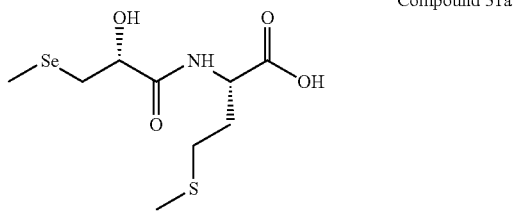

Compound 31a

Compound 31a is obtained using the conditions of Example D10.2, starting with 89 mg of compound 30a.

The yield consists of 82 mg (99%) of the desired product in the form of a colorless oil.

¹H NMR (CDCl₃, 400 MHz): δ (ppm)=2.08 (s, 3H); 2.11 (m, 1H); 2.15 (s, 3H); 2.28 (m, 1H); 2.63 (m, 2H); 2.91 (dd, J=13.0 Hz, J=7.0 Hz, 1H); 3.08 (dd, J=13.0 Hz, J=4.0 Hz, 1H); 4.39 (dd, J=7.0 Hz, J=4.0 Hz, 1H); 4.74 (m, 1H); 7.59 (d, J=8.0 Hz, 1H).

Example D12

Preparation of [(2S)-2-hydroxy-3-methylselenopropanoyl]-(S)-methionine (Compound 31b)

D12.1. Preparation of the methyl ester of [(2S)-2-hydroxy-3-methylselenopropanoyl]-(S)-methionine (Compound 30b)

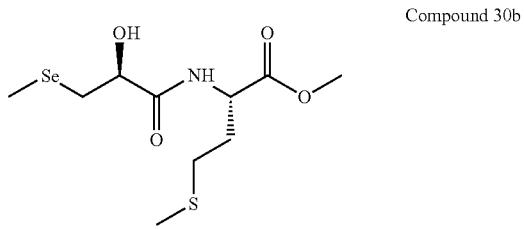

Compound 30b

Compound 30b is obtained using the conditions of Example D9, starting with 100 mg (535 μmol; 1 eq.) of (S)-2-hydroxy-3-(methylseleno)propanoic acid (12) and 112 mg (535 μmol; 1 eq.) of the methyl ester of the hydrochloride of (S)-methionine. The yield consists of 115 mg (57%) of the desired product in the form of a colorless oil.

¹H NMR (CDCl₃, 400 MHz): δ (ppm)=2.04 (s, 3H); 2.07 (m, 1H); 2.13 (s, 3H); 2.23 (m, 1H); 2.57 (t, J=7.5 Hz, 2H); 2.92 (dd, J=13.0 Hz, J=8.0 Hz, 1H); 3.10 (dd, J=13.0 Hz, J=4.5 Hz, 1H); 3.42 (d, J=4.5 Hz, 1H); 3.79 (s, 3H); 4.22 (m, 1H); 4.75 (m, 1H); 7.35 (d, J=8.0 Hz, 1H).

D12.2. Preparation of [(2S)-2-hydroxy-3-methylselenopropanoyl]-(S)-methionine (Compound 31b)

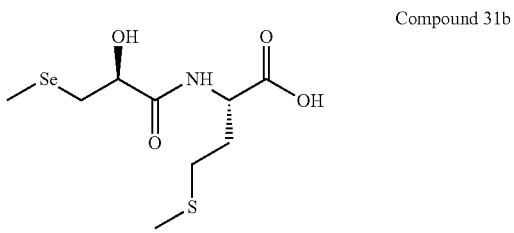 [SMILES: CSCC[C@H](NC(=O)[C@H](O)C[Se]C)C(=O)O]

Compound 31b

Compound 31 b is obtained using the conditions of Example D10.2, starting with 115 mg of compound 30b.

The yield consists of 98 mg (98%) of the desired product in the form of a yellow oil.

¹H NMR (CDCl₃, 400 MHz): δ (ppm)=2.05 (s, 3H); 2.10 (m, 1H); 2.15 (s, 3H); 2.28 (m, 1H); 2.62 (t, J=7.5 Hz, 2H); 2.91 (dd, J=13.0 Hz, J=8.0 Hz, 1H); 3.11 (dd, J=13.5 Hz, J=4.5 Hz, 1H); 4.27 (dd, J=8.0 Hz, J=4.5 Hz, 1H); 4.75 (m, 1H); 7.48 (d, J=8.0 Hz, 1H).

Example D13

Preparation of the methyl ester of N(α)-[(2RS)-2-hydroxy-3-methylselenopropanoyl]-N(ω)-tert-butoxycarbonyl-(S)-lysine (Compound 32)

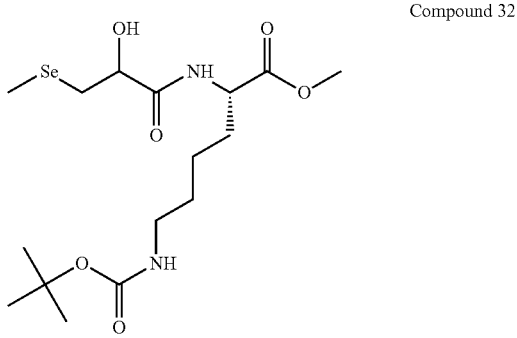

Compound 32

Compound 32 is obtained using the conditions of Example D9, starting with 100 mg (535 µmol; 1 eq.) of 2-hydroxy-3-(methylseleno)propanoic acid (10) and 162 mg (546 µmol; 1 eq.) of the methyl ester of the hydrochloride of N(ω)-tert-butoxycarbonyl-(S)-lysine.

The yield consists of 171 mg (73%) of the desired product in the form of a colorless oil.

$^1$H NMR (CDCl$_3$, 400 MHz) 50/50 mixture of 2 diastereoisomers (R,S) and (S,S): δ (ppm)=1.37 (m, 2H); 1.44 (s, 9H); 1.48 (m, 2H); 1.73 (m, 1H); 1.89 (m, 1H); 2.02 and 2.04 (2s, 3H); 2.89 (m, 1H); 3.07 (m, 3H); 3.74 and 3.75 (s, 3H); 3.85 (m, 1H); 4.26 (m, 1H); 4.59 (m, 1H); 4.69 (m, 1H); 7.30 (m, 1H).

UPLC-MS (AP+): 449.0 (M+Na)$^+$

Example D14

Preparation of the methyl ester of N(α)-[(2RS)-2-hydroxy-3-methylselenopropanoyl]-N(ω)-fluoroenylmethyloxycarbonyl-(S)-lysine (Compound 33)

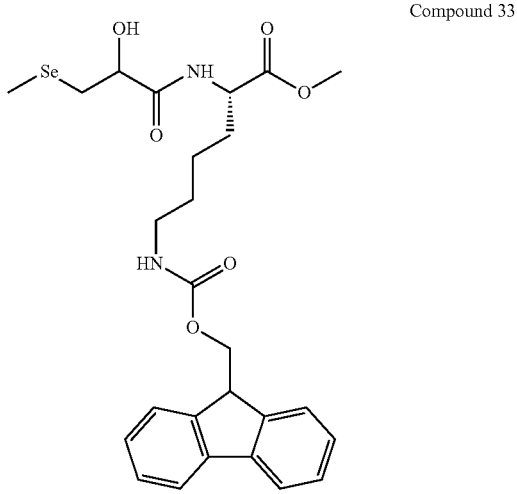

Compound 33

Compound 33 is obtained using the conditions of Example D9, starting with 200 mg (1.059 mmol; 1 eq.) of 2-hydroxy-3-(methylseleno)propanoic acid (10) and 448 mg (1.059 mmol; 1 eq.) of the methyl ester of the hydrochloride of N(ω)-fluorenylmethyloxycarbonyl-(S)-lysine.

The yield consists of 430 mg (59%) of the desired product in the form of a colorless oil.

$^1$H NMR (CDCl$_3$, 400 MHz): δ (ppm)=1.42 (m, 2H); 1.58 (m, 2H); 1.76 (m, 2H); 1.91 (m, 1H); 2.03 (s, 3H); 2.92 (m, 1H); 3.10 (m, 1H); 3.21 (m, 2H); 3.78 (s, 3H); 4.25 (m, 2H); 4.43 (m, 2H); 4.64 (m, 1H); 4.90 (m, 1N); 7.25 (m, 1H); 7.35 (m, 2H); 7.42 (m, 2H); 7.63 (m, 2H); 7.80 (m, 2H).

UPLC-MS (AP+): 571.3 (M+Na)$^+$

Example D15

Preparation of the benzyl ester of N(α)-[(2RS)-2-hydroxy-3-methylselenopropanoyl]-N(ω)-benzyloxycarbonyl-(S)-lysine (Compound 34)

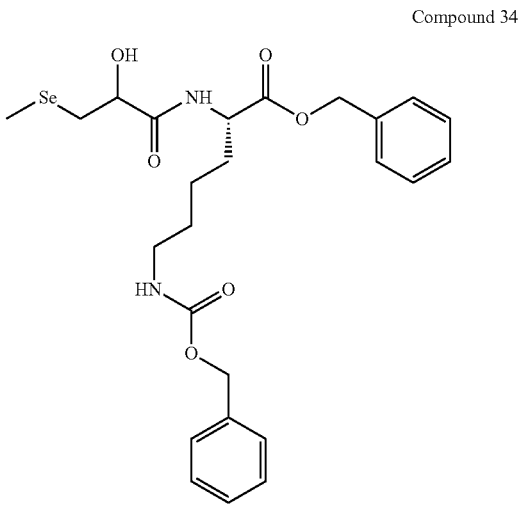 [SMILES: C[Se]CC(O)C(=O)N[C@@H](CCCCNC(=O)OCc1ccccc1)C(=O)OCc1ccccc1]

Compound 34

Compound 34 is obtained using the conditions of Example D9, starting with 400 mg (2.12 mmol; 1 eq.) of 2-hydroxy-3-(methylseleno)propanoic acid (10) and 862 mg (2.12 mmol; 1 eq.) of the benzyl ester of the hydrochloride of N(ω)-benzyloxycarbonyl-(S)-lysine.

The yield consists of 944 mg (76%) of the desired product in the form of a yellow oil.

$^1$H NMR (CDCl$_3$, 400 MHz) 50/50 mixture of 2 diastereoisomers 34a (R,S) and 34b (S,S): δ (ppm): 1.35 (m, 2H); 1.51 (m, 2H); 1.75 (m, 2H); 1.91 (m, 1H); 2.00 and 2.03 (2s, 3H); 2.89 (m, 1H); 3.07 (m, 1H); 3.17 (m, 2H); 3.37 and 3.49 (2s, 1H); 4.23 (m, 1H); 4.67 (m, 1H); 4.81 (m, 1H); 5.12-5.26 (m, 4H); 7.33-7.43 (m, 10H).

Example D16

Preparation of [(2RS)-2-hydroxy-3-methylselenopropanoyl]-(S)-(Compound 36) D16.1. Preparation of the methyl ester of [(2RS)-2-hydroxy-3-methylselenopropanoyl]-(S)-selenomethionine (Compound 35)

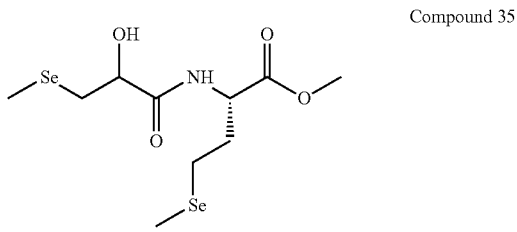

Compound 35

Compound 35 is obtained using the conditions of Example D9, starting with 136 mg (720 µmol; 1 eq.) of 2-hydroxy-3-(methylseleno)propanoic acid (10) and 187 mg (720 µmol; 1 eq.) of the methyl ester of the hydrochloride of (S)-selenomethionine.

The yield consists of 180 mg (63%) of the desired product in the form of a colorless oil.

¹H NMR (CDCl₃, 400 MHz) 50/50 mixture of 2 diastereoisomers 35a (R,S) and 35b (S,S): δ (ppm): 2.03 (s, 3H); 2.04 and 2.07 (2s, 3H); 2.13 (m, 1H); 2.28 (m, 1H); 2.57 (t, J=7.5 Hz, 2H); 2.92 (m, 1H); 3.10 (m, 1H); 3.38 (m, 1H); 3.79 and 3.80 (2s, 3H); 4.25 (m, 1H); 4.75 (m, 1H); 7.33 and 7.37 (2d, J=8.5 Hz, 1H).

D16.2. Preparation of [(2RS)-2-hydroxy-3-methylselenopropanoyl]-(S)-selenomethionine (Compound 36)

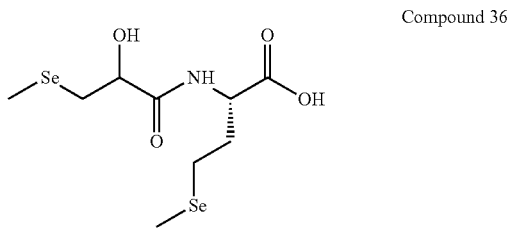 [SMILES: C[Se]CC[C@H](NC(=O)C(O)C[Se]C)C(=O)O]

Compound 36

Compound 36 is obtained using the conditions of Example B1, starting with 130 mg of compound 35.

After 16 h of stirring at ambient temperature, the reaction medium is diluted in water (20 mL), then extracted with ethyl acetate (2×10 mL). The pH of the medium is adjusted to 1 by adding a 2 M hydrochloric acid aqueous solution. The medium is extracted with ethyl acetate (3×10 mL). The organic phases of this second extraction are combined, dried over Na₂SO₄, filtered and concentrated.

The yield consists of 112 mg (89%) of the desired product in the form of a yellow oil.

¹H NMR (CDCl₃, 400 MHz) 50/50 mixture of 2 diastereoisomers 36a (R,S) and 36b (S,S): δ (ppm): 2.05 (s, 3H); 2.08 (s, 3H); 2.17 (m, 1H); 2.33 (m, 1H); 2.63 (m, 2H); 2.92 (m, 1H); 3.10 (m, 1H); 4.26 and 4.35 (2dd, J=8.0 Hz, J=4.5 Hz, 1H); 4.75 (m, 1H); 7.43 and 7.49 (2d, J=8.0 Hz, 1H).

Example D17

Preparation of [(2R)-2-hydroxy-3-methylselenopropanoyl]-(S)-selenomethionine (Compound 36a)

D17.1. Preparation of the methyl ester of [(2R)-2-hydroxy-3-methylselenopropanoyl]-S-selenomethionine (Compound 35a)

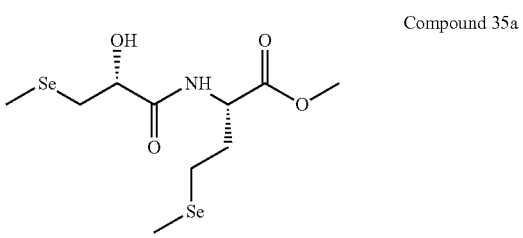

Compound 35a

Compound 35a is obtained using the conditions of Example D9, starting with 185 mg (950 µmol; 1 eq.) of (R)-2-hydroxy-3-(methylseleno)propanoic acid (11) and 260 mg (950 µmol; 1 eq.) of the methyl ester of the hydrochloride of (S)-selenomethionine.

The yield consists of 233 mg (62%) of the desired product in the form of a pale yellow oil.

¹H NMR (CDCl₃, 400 MHz): δ (ppm)=2.03 (s, 3H); 2.07 (s, 3H); 2.12 (m, 1H); 2.29 (m, 1H); 2.57 (m, 2H); 2.93 (dd, J=13.0 Hz, J=7.5 Hz, 1H); 3.09 (dd, J=13.0 Hz, J=4.5 Hz, 1H); 3.32 (m, 1H); 3.80 (s, 3H); 4.27 (m, 1H); 4.75 (m, 1H); 7.37 (d, J=8.0 Hz, 1H).

D17.2. Preparation of [(2R)-2-hydroxy-3-methylselenopropanoyl]-(S)-selenomethionine (Compound 36a)

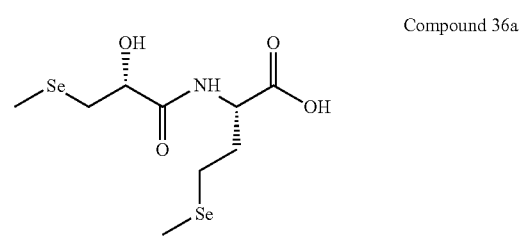 [SMILES: C[Se]CC[C@H](NC(=O)[C@@H](O)C[Se]C)C(=O)O]

Compound 36a

Compound 36a is obtained using the conditions of Example B1, starting with 183 mg of compound 35a.

The reaction medium is diluted in water (20 mL), then extracted with ethyl acetate (2×10 mL). The pH of the medium is adjusted to 1 by adding a 2 M hydrochloric acid aqueous solution. The medium is extracted with ethyl acetate (3×10 mL). The organic phases are combined, dried over Na₂SO₄, filtered and concentrated.

The yield consists of 178 mg (100%) of the desired product in the form of a cream colored solid.

¹H NMR (CDCl₃, 400 MHz): δ (ppm)=2.05 (s, 3H); 2.08 (s, 3H); 2.18 (m, 1H); 2.35 (m, 1H); 2.64 (m, 2H); 2.91 (dd, J=13.0 Hz, J=7.0 Hz, 1H); 3.09 (dd, J=13.0 Hz, J=4.0 Hz, 1H); 4.38 (dd, J=7.0 Hz, J=4.0 Hz, 1H); 4.74 (m, 1H); 7.53 (d, J=8.0 Hz, 1H).

Example D18

Preparation of the methyl ester of [(2S)-2-hydroxy-3-methylselenopropanoyl]-(S)-selenomethionine (Compound 36b)

D18.1. Preparation of the methyl ester of [(2S)-2-hydroxy-3-methylselenopropanoyl]-(S)-selenomethionine (Compound 35b)

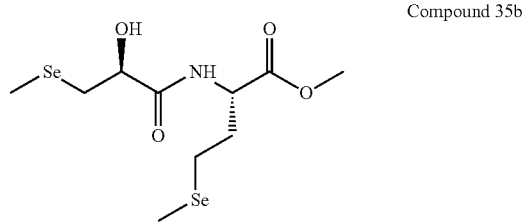

Compound 35b

Compound 35b is obtained using the conditions of Example D9, starting with 177 mg (949 μmol; 1 eq.) of (S)-2-hydroxy-3-(methylseleno)propanoic acid (12) and 260 mg (950 μmol; 1 eq.) of the methyl ester of the hydrochloride of (S)-selenomethionine.

The yield consists of 236 mg (58%) of the desired product in the form of a pale yellow oil.

$^1$H NMR (CDCl$_3$, 400 MHz): δ (ppm)=2.03 (s, 3H); 2.04 (s, 3H); 2.12 (m, 1H); 2.29 (m, 1H); 2.57 (t, J=7.5 Hz, 2H); 2.92 (dd, J=13.0 Hz, J=8.0 Hz, 1H); 3.10 (dd, J=13.0 Hz, J=4.5 Hz, 1H); 3.79 (s, 3H); 4.22 (dd, J=8.0 Hz, J=4.5 Hz, 1H); 4.75 (m, 1H); 7.33 (d, J=8.5 Hz, 1H).

D18.2. Preparation of [(2S)-2-hydroxy-3-methylselenopropanoyl]-(S)-selenomethionine (Compound 36b)

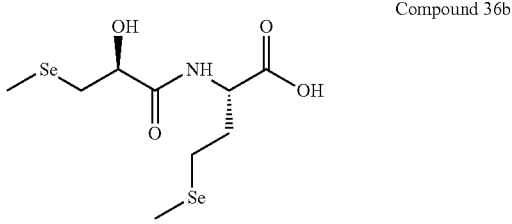 [SMILES: C[Se]CC[C@H](NC(=O)[C@H](O)C[Se]C)C(=O)O]

Compound 36b

Compound 36b is obtained using the conditions of Example B1, starting with 186 mg of compound 35b.

After 16 h of stirring at ambient temperature, the reaction medium is diluted in water (20 mL), then extracted with ethyl acetate (2×10 mL). The pH of the medium is adjusted to 1 by adding a 2 M hydrochloric acid aqueous solution. The medium is extracted with ethyl acetate (3×10 mL). The organic phases are combined, dried over Na$_2$SO$_4$, filtered and concentrated. The residue is purified on a silica column (cyclohexane/ethyl acetate, then dichloromethane/methanol). The oil obtained is triturated with cyclohexane, then with pentane, dissolved in TBME and dichloromethane, then concentrated to dryness.

The yield consists of 90 mg (50%) of the desired product in the form of a yellow oil.

$^1$H NMR (CDCl$_3$, 400 MHz): δ (ppm)=2.05 (s, 6H); 2.19 (m, 1H); 2.34 (m, 1H); 2.63 (m, 2H); 2.91 (dd, J=13.5 Hz, J=8.0 Hz, 1H); 3.12 (dd, J=13.5 Hz, J=4.5 Hz, 1H); 4.26 (dd, J=8.0 Hz, J=4.5 Hz, 1H); 4.75 (m, 1H); 7.41 (d, J=8.0 Hz, 1H).

4—Preparation of the Compounds E: 2-acyloxy-3-(alkylseleno)propanoic acids and corresponding esters The Compounds E are prepared either in one step by reacting the compounds B with carboxylic anhydrides, or in two steps from the compounds A by reactions with carboxylic anhydrides, followed by hydrolysis.

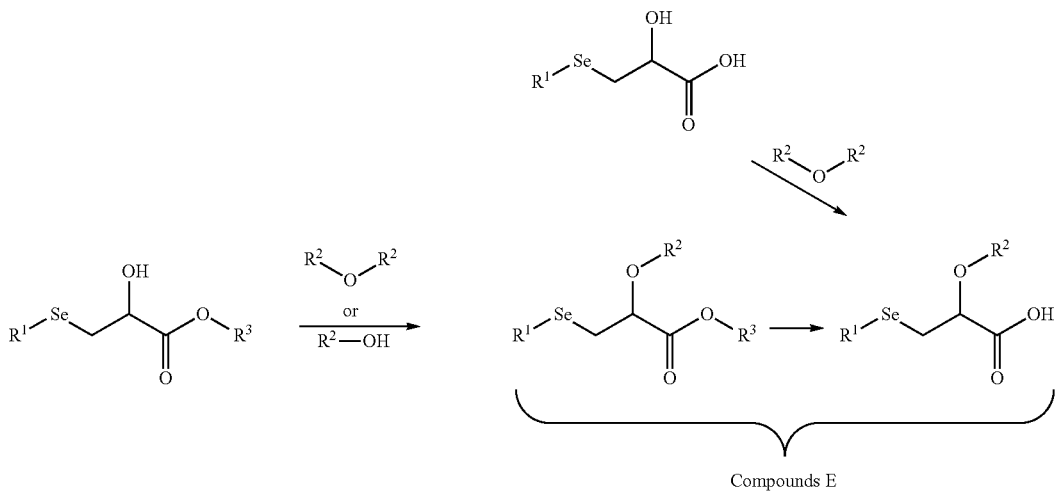

Compounds E

Example E1

Preparation of 2-(acetyloxy)-3-(methylseleno)propanoic acid (Compound 37)

Compound 37

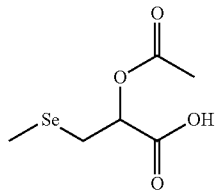

374 mg (2 mmol) of 2-hydroxy-3-(methylseleno)propanoic acid (10) are dissolved under nitrogen in 33 mL of dichloromethane. 817 mg (756 µL; 8 mmol; 4 eq.) of acetic anhydride, then 2.5 mg (20 µmol; 0.01 eq.) of 4-dimethylaminopyridine are added to the medium. The medium is left under stirring under nitrogen and at ambient temperature for 6 h.

817 mg (756 µL; 8 mmol; 4 eq.) of acetic anhydride are again added to the medium. The medium is stirred under nitrogen and at ambient temperature for 16 h.

10 mL of water are added, then the dichloromethane is eliminated from the medium by evaporation. 40 mL of a saturated $NH_4Cl$ aqueous solution are added, then the medium is extracted with ethyl acetate (3×40 mL). The organic phases are combined, dried with $Na_2SO_4$, filtered and concentrated. The oil obtained is purified on a silica column (cyclohexane/ethyl acetate with 1% TFA). The yield consists of 292 mg (63%) of compound 37 in the form of a yellow oil.

$^1$H NMR (CDCl$_3$, 400 MHz): δ (ppm): 2.15 (s, 3H); 2.20 (s, 3H); 2.97 (dd, J=13.5 Hz, J=7.5 Hz, 1H); 3.04 (dd, J=13.5 Hz, J=4.5 Hz, 1H); 5.37 (dd, J=7.5 Hz, J=4.5 Hz, 1H); 9.90 (s, 1H).

$^{13}$C NMR (CDCl$_3$, 75 MHz): δ (ppm): 6.2; 21.0; 25.0; 72.6; 170.7

UPLC-MS (AP−): 224.7 (M−H$^+$)

Example E2

Preparation of 2-(dodecanoyloxy)-3-(methylseleno)propanoic acid (Compound 38)

Compound 38

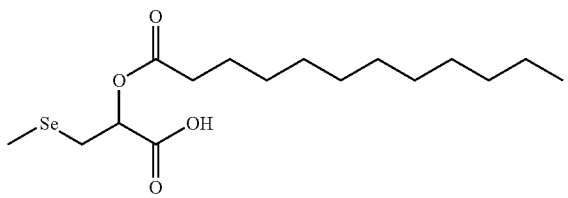

400 mg (2.14 mmol) of 2-hydroxy-3-(methylseleno)propanoic acid (10) are dissolved under nitrogen in 35 mL of dichloromethane. 3.344 g (8.56 mmol; 4 eq.) of lauric anhydride, then 2.6 mg (21 µmol; 0.01 eq.) of 4-dimethylaminopyridine are added to the medium. The medium is stirred under nitrogen and at ambient temperature for 6 h.

3.344 g (8.56 mmol; 4 eq.) of lauric anhydride are added again to the medium. The medium is stirred under nitrogen and at ambient temperature for 16 h.

10 mL of water are added, then the medium is concentrated to dryness. The residue is purified on a silica column (cyclohexane/ethyl acetate, then dichloromethane/methanol). The yield consists of 394 mg (47%) of compound 38 in the form of a yellow oil.

$^1$H NMR (CDCl$_3$, 400 MHz): δ (ppm): 0.91 (m, 3H); 1.29 (m, 16H); 1.68 (m, 2H); 2.13 (s, 3H); 2.44 (t, J=7.5 Hz, 2H); 3.00 (m, 2H); 5.30 (m, 1H).

Example E3

Preparation of 2-(benzoyloxy)-3-(methylseleno)propanoic acid (Compound 40)

Example 3.1

Preparation of the methyl ester of 2-(benzoyloxy)-3-(methylseleno)propanoic acid (Compound 39)

Compound 39

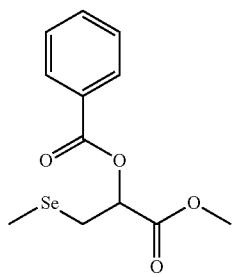

500 mg (2.46 mmol) of compound 1 are dissolved under nitrogen in 40 mL of dichloromethane. 1.136 g (4.92 mmol; 2 eq.) of benzoic anhydride, then 30 mg (246 µmol; 0.1 eq.) of 4-dimethylaminopyridine are added to the medium. The medium is stirred under nitrogen at ambient temperature for 25 h.

The medium is concentrated to dryness. The residue is purified on a silica column (cyclohexane/ethyl acetate). The yield consists of 633 mg (81%) of compound 39 in the form of a colorless oil.

$^1$H NMR (CDCl$_3$, 400 MHz): δ (ppm)=2.17 (s, 3H); 3.13 (m, 2H); 3.83 (s, 3H); 5.60 (t, J=6.0 Hz, 1H); 7.50 (t, J=7.5 Hz, 2H); 7.63 (t, J=7.5 Hz, 1H); 8.13 (d, J=7.5 Hz, 2H).

E3.2: Preparation of 2-(benzoyloxy)-3-(methylseleno)propanoic acid (Compound 40)

Compound 40

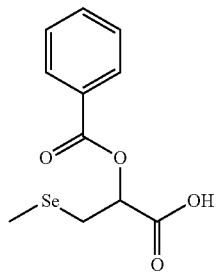

Compound 40 is obtained using the conditions of Example B1, starting with 372 mg of compound 39.

After 16 h of stirring at ambient temperature, the reaction medium is diluted in water (10 mL), then extracted with ethyl acetate (2×10 mL). The pH of the medium is adjusted to 1 by adding a 2 M hydrochloric acid aqueous solution. The medium is extracted with ethyl acetate (3×10 mL). The organic phases of this second extraction are combined, dried over $Na_2SO_4$, filtered and concentrated.

The yield consists of 283 mg (81%) of the desired product in the form of a white solid.

$^1$H NMR (CDCl$_3$, 400 MHz): δ (ppm)=2.13 (s, 3H); 2.99 (dd, J=13.5 Hz, J=6.0 Hz, 1H); 3.09 (dd, J=13.5 Hz, J=4.5 Hz, 1H); 4.58 (dd, J=6.0 Hz, J=4.5 Hz, 1H); 7.52 (t, J=7.5 Hz, 2H); 7.66 (t, J=7.5 Hz, 1H); 8.15 (d, J=7.5 Hz, 2H).

Example E4

Preparation of the methyl ester of 3-(methylseleno)-2-[(3'-pyridine)oxycarbonyl]propanoic acid (Compound 41)

Compound 41

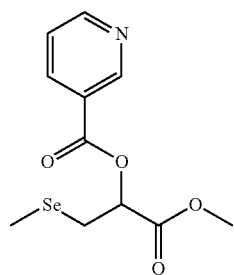

384 mg (1.85 mmol) of compound 1 are dissolved under nitrogen in 30 mL of dichloromethane. 872 mg (3.7 mmol; 2 eq.) of 3-pyridinecarboxylic anhydride, then 23 mg (185 μmol; 0.1 eq.) of 4-dimethylaminopyridine are added to the medium. The medium is stirred under nitrogen and at ambient temperature for 18 h. The medium is filtered through fritted glass, then the filtrate is concentrated to dryness. The residue is purified on a silica column (cyclohexane/ethyl acetate).

The yield consists of 490 mg (83%) of compound 41 in the form of a colorless oil.

$^1$H NMR (CDCl$_3$, 400 MHz): δ (ppm)=2.16 (s, 3H); 3.13 (m, 2H); 3.84 (s, 3H); 5.60 (dd, J=7.0 Hz, J=5.0 Hz, 1H); 7.47 (dd, J=8.0 Hz, J=5.0 Hz, 1H); 8.39 (d, J=8.0 Hz, 1H); 8.85 (d, J=5.0 Hz, 1H); 9.31 (s, 1H).

Example E5

Preparation of 2-[(tert-butoxycarbonyl)oxy]-3-(methylseleno)propanoic acid (Compound 43)

E5.1: Preparation of the methyl ester of 2-[(tert-butoxycarbonyl)oxy]-3-(methylseleno)propanoic acid (Compound 42)

Compound 42

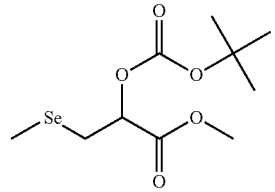

100 mg (507 μmol) of compound 1 are dissolved in 5 mL of ethyl acetate. The medium is cooled to 10° C., then 103 mg (143 μL; 1.01 mmol; 2 eq.) of triethylamine are added dropwise. 120 mg (533 μmol; 1.05 eq.) of di-tert-butyl dicarbonate dissolved in 1 mL of ethyl acetate are added rapidly dropwise. The medium is heated at 90° C. for 48 h.

The reaction medium is diluted with ethyl acetate (25 mL), then the medium is washed with a 5% citric acid aqueous solution (2×10 mL), then with a saturated NaCl aqueous solution (10 mL). The organic phase is dried over $Na_2SO_4$, filtered and concentrated. The residue is purified on a silica column (cyclohexane/ethyl acetate).

The yield consists of 101 mg (63%) of compound 42 in the form of a colorless oil.

$^1$H NMR (CDCl$_3$, 400 MHz): δ (ppm)=1.55 (s, 9H); 2.13 (s, 3H); 2.94 (dd, J=13.5 Hz, J=7.5 Hz, 1H); 3.00 (dd, J=13.5 Hz, J=5.0 Hz, 1H); 3.82 (s, 3H); 5.17 (dd, J=7.5 Hz, J=5.0 Hz, 1H).

E5.2: Preparation of 2-[(tert-butoxycarbonyl)oxy]-3-(methylseleno)propanoic acid (Compound 43)

Compound 43

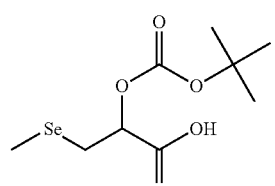

Compound 43 is obtained using the conditions of Example B1, starting with 363 mg of compound 42.

After 16 h of stirring at ambient temperature, the reaction medium is diluted in water (25 mL), then extracted with ethyl acetate (2×20 mL). The pH of the medium is adjusted to 4 by adding a 5% citric acid aqueous solution (2×10 mL). The medium is extracted with ethyl acetate (5×25 mL). The organic phases of the second extraction are combined, dried over Na$_2$SO$_4$, filtered and concentrated.

The residue is purified on a silica column (dichloromethane/methanol), then purified again on a silica column (cyclohexane/ethyl acetate).

The yield consists of 39 mg (11%) of the desired product in the form of a colorless oil.

$^1$H NMR (CDCl$_3$, 400 MHz): δ (ppm)=1.52 (s, 9H); 2.14 (s, 3H); 2.96 (dd, J=13.5 Hz, J=7.5 Hz, 1H); 3.03 (dd, J=13.5 Hz, J=4.5 Hz, 1H); 5.20 (dd, J=7.5 Hz, J=4.5 Hz, 1H); 10.04 (s, 1H).

Example E6

Preparation of the methyl ester of (2RS)—[N-(tert-butoxycarbonyl)-S-methionyl]-3-methylselenopropanoic acid (Compound 44)

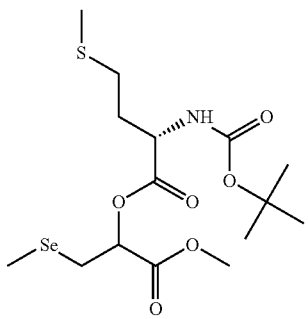

Compound 44

500 mg (2.0 mmol) of BOC—(S)-methionine are dissolved in 25 mL of dichloromethane. 417 mg (2.0 mmol; 1 eq.) of N,N'-dicyclohexylcarbodiimide are added. The medium is stirred for 10 min at ambient temperature, then 416 mg (2.0 mmol; 1 eq.) of compound 1 and 25 mg (200 μmol; 0.1 eq.) of 4-dimethylaminopyridine are added. The mixture is stirred at ambient temperature for 16 h.

The medium is concentrated to dryness. The residue is purified on a silica column (cyclohexane/ethyl acetate).

The yield consists of 709 mg (78%) of compound 44 in the form of a colorless oil.

$^1$H NMR (CDCl$_3$, 400 MHz) 50/50 mixture of 2 diastereoisomers 44a (R,S) and 44b (S,S): δ (ppm)=1.48 (s, 9H); 2.04 (m, 1H); 2.12 and 2.14 (2s, 3H); 2.15 and 2.16 (2s, 3H); 2.26 (m, 1H); 2.65 (m, 2H); 2.99 (m, 2H); 3.80 and 3.81 (2s, 3H); 4.58 (m, 1H); 5.17 (m, 1H); 5.39 (m, 1H).

UPLC-MS (AP+): 451.9 (M+Na)$^+$

Example E7

Preparation of the methyl ester of 4-methylseleno-2-(2'-acetyloxy-3'-methylselenopropanoyl)butyric acid (Compound 45) and 4-methylseleno-2-(2'-acetyloxy-3'-methylselenopropanoyl)butyric acid (Compound 46)

E7.1. Preparation of the methyl ester of 4-methylseleno-2-(2'-acetyloxy-3'-methylselenopropanoyl) butyric acid (Compound 45)

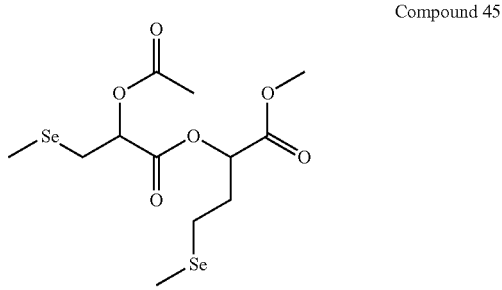

Compound 45

128 mg (522 μmol) of 2-(acetyloxy)-3-(methylseleno) propanoic acid (37) are dissolved under nitrogen in 5 mL of dichloromethane. 108.7 mg (522 μmol) of N,N'-dicyclohexylcarbodiimide are added to the medium. The medium is stirred under nitrogen and at ambient temperature for 10 min. 116 mg (522 μmol) of methyl 2-hydroxy-4-(methylseleno)butanoate (EP1778706, prepared in a similar manner to Example 9 using methanol instead of ethanol) in solution in 5 mL of dichloromethane, then 6.4 mg (52 μmol; 0.01 eq.) of 4-dimethylaminopyridine are added. The medium is stirred at ambient temperature for 16 h.

The medium is concentrated to dryness. The residue is purified on a silica column (cyclohexane/ethyl acetate).

The yield consists of 189 mg (77%) of compound 45 in the form of a colorless oil.

$^1$H NMR (CDCl$_3$, 400 MHz) mixture of 2 diastereoisomers: δ (ppm)=2.03 and 2.04 (2s, 3H); 2.15 and 2.16 (2s, 3H); 2.20 (s, 3H); 2.23-2.3 (m, 2H); 2.54-2.7 (m, 2H); 2.95-3.02 (m, 1H); 3.11 (dd, J=13.5 Hz, J=4.0 Hz, 1H); 3.79 and 3.80 (2s, 3H); 5.15 to 5.45 (m, 2H).

UPLC-MS (AP+): 442.9 (M+Na)$^+$

E7.2. Preparation of 4-methylseleno-2-(2'-acetyloxy-3'-methylselenopropanoyl)butyric acid (Compound 46) by hydrolysis of the methyl ester

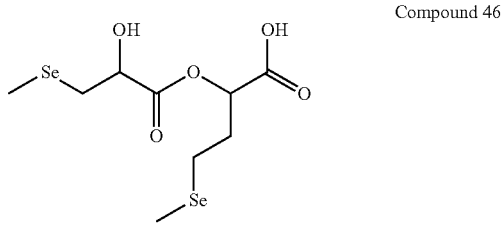 [SMILES: C[Se]CCC(OC(=O)C(O)C[Se]C)C(=O)O]

Compound 46

Compound 46 is obtained using the conditions of Example B1, starting with 180 mg of compound 45.

After 16 h of stirring at ambient temperature, the reaction medium is diluted in water (20 mL), then extracted with ethyl acetate (2×5 mL). The aqueous phase is lyophilized. The lyophilizate is redissolved with a 4 N hydrochloric acid solution in dioxane. The medium is stirred for 10 min and then concentrated to dryness. The concentrate is redissolved in 10 mL of water, then the solution is lyophilized.

The yield consists of 138 mg (71%) of the desired product containing 2 LiCl in the form of a yellow sticky solid.

$^1$H NMR (D$_2$O, 400 MHz): δ (ppm)=2.00 (s, 3H); 2.05 (s, 3H); 2.07-2.24 (m, 2H); 2.65 (m, 2H); 2.89 (dd, J=13.0 Hz, J=6.5 Hz, 1H); 3.00 (dd, J=13.0 Hz, J=4.5 Hz, 1H); 4.36 (dd, J=8.0 Hz, J=4.0 Hz, 1H); 4.50 (dd, J=6.5 Hz, J=4.5 Hz, 1H).

Example E8

Preparation of 3-methylseleno-2-(2'-hydroxy-4'-methylselenobutanoyl)propanoic acid (Compound 48)

E8.1: Preparation of the methyl ester of 3-methylseleno-2-(2'-hydroxy-4'-methylselenobutanoyl)propanoic acid (Compound 47)

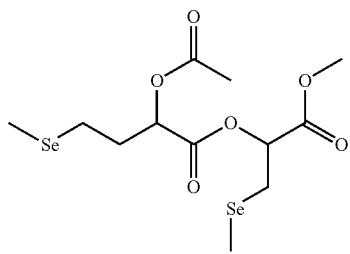

Compound 47

Compound 47 is obtained using the conditions of Example E7, starting with 89 mg of 2-acetyloxymethylselenobutyric acid (EP1778706, Example 11) and 72 mg of compound 1.

The medium is filtered through fritted glass, then the filtrate is concentrated to dryness. The residue is purified on a silica column (cyclohexane/ethyl acetate).

The yield consists of 97 mg (60%) of the desired product in the form of a colorless oil.

$^1$H NMR (CDCl$_3$, 400 MHz) mixture of diastereoisomers: δ (ppm)=2.05 and 2.06 (2s, 3H); 2.11 and 2.14 (2s, 3H); 2.18 and 2.19 (2s, 3H); 2.27-2.37 (m, 2H); 2.60-2.80 (m, 2H); 2.92-3.07 (m, 2H); 3.80 and 3.81 (2s, 3H); 5.24 (dd, J=12.5 Hz, J=6.0 Hz, 1H); 5.34 and 5.45 (2dd, J=8.0 Hz, J=4.5 Hz, 1H).

UPLC-MS (AP+): 443.0 (M+Na)$^+$

E8.2: Preparation of 3-methylseleno-2-(2'-hydroxy-4'-methylselenobutanoyl)propanoic acid (Compound 48)

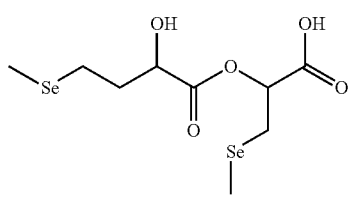

Compound 48

Compound 48 is obtained using the conditions of Example E7.2, starting with 79 mg of compound 47.

The yield consists of 69 mg (84%) of the desired product containing 2 LiCl in the form of a colorless sticky solid.

$^1$H NMR (D$_2$O, 400 MHz): δ (ppm)=2.04 (m, 3H); 2.09-2.14 (m, 3H); 2.20-2.27 (m, 2H); 2.64-2.74 (m, 2H); 2.93 (dd, J=13.0 Hz, J=6.5 Hz, 1H); 3.04 (dd, J=13.5 Hz, J=4.5 Hz, 1H); 4.55 (dd, J=6.5 Hz, J=4.5 Hz, 1H); 5.05 (m, 1H).

Example E9

Preparation of 2-(pentanoyloxy)-3-(methylseleno)propanoic acid (Compound 49)

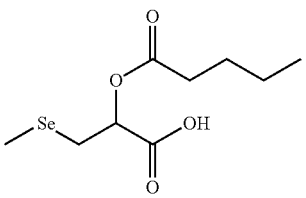

Compound 49

407 mg (1.98 mmol) of 2-hydroxy-3-(methylseleno)propanoic acid (10) are dissolved under nitrogen in 33 mL of dichloromethane. 752 mg (817 μL; 3.96 mmol; 2 eq.) of valeric anhydride, then 2.4 mg (19.8 μmol; 0.01 eq.) of 4-dimethylaminopyridine are added to the medium. The medium is stirred under nitrogen and at ambient temperature for 24 h.

752 mg (817 μL; 3.96 mmol; 2 eq.) of valeric anhydride, then 2.4 mg (19.8 μmol; 0.01 eq.) of 4-dimethylaminopyridine are again added to the medium. The medium is stirred under nitrogen and at ambient temperature for 48 h. 10 mL of water are added, then the dichloromethane is eliminated from the medium by evaporation. 25 mL of a saturated NH$_4$C aqueous solution are added, then the medium is extracted with ethyl acetate (3×10 mL). The organic phases are combined, dried with Na$_2$SO$_4$, filtered and concentrated. The oil obtained is purified on a silica column (cyclohexane/ethyl acetate). The yield consists of 260 mg (48%) of compound 49 in the form of a colorless oil.

$^1$H NMR (CDCl$_3$, 400 MHz): δ (ppm)=0.96 (t, J=7.4 Hz, 3H); 1.42 (m, 2H); 1.69 (m, 2H); 2.15 (s, 3H); 2.46 (td, J=1.9 Hz, J=7.4 Hz, 2H); 3.01 (m, 2H); 5.36 (dd, J=4.3 Hz, J=7.6 Hz, 1H).

UPLC-MS (AP−): 267.3 (M−H$^+$)

Example E10

Preparation of 2-(nonanoyloxy)-3-(methylseleno)propanoic acid (Compound 50)

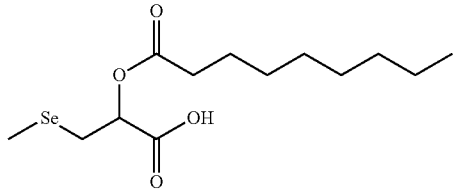

Compound 50

260 mg (1.39 mmol) of 2-hydroxy-3-(methylseleno)propanoic acid (10) are dissolved under nitrogen in 23 mL of dichloromethane. 874 mg (963 µL; 2.78 mmol; 2 eq.) of nonanoic anhydride, then 1.7 mg (13.9 µmol; 0.01 eq.) of 4-dimethylaminopyridine are added to the medium. The medium is stirred under nitrogen and at ambient temperature for 24 h.

874 mg (963 µL; 2.78 mmol; 2 eq.) of nonanoic anhydride, then 1.7 mg (13.9 µmol; 0.01 eq.) of 4-dimethylaminopyridine are added to the medium. The medium is stirred under nitrogen and at ambient temperature for 24 h.

10 mL of water are added, then the dichloromethane is eliminated from the medium by evaporation. 25 mL of a saturated $NH_4Cl$ aqueous solution are added, then the medium is extracted with ethyl acetate (3×10 mL). The organic phases are combined, dried with $Na_2SO_4$, filtered and concentrated. The oil obtained is purified on a silica column (cyclohexane/ethyl acetate). The yield consists of 116 mg (25%) of compound 50 in the form of a colorless oil.

$^1$H NMR ($CDCl_3$, 400 MHz): δ (ppm)=0.91 (t, J=6.9 Hz, 3H); 1.34 (m, 10H); 1.70 (m, 2H); 2.14 (s, 3H); 2.45 (td, J=1.7 Hz, J=7.4 Hz, 2H); 3.01 (m, 2H); 5.37 (dd, J=4.3 Hz, J=7.6 Hz, 1H).

UPLC-MS (AP−): 322.9 (M−H$^+$)

Example E11.1

Preparation of the methyl ester of 2-(linoleoyloxy)-3-(methylseleno)propanoic acid (Compound 51)

Compound 51

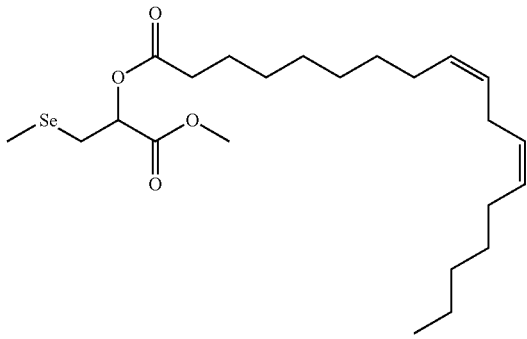

818 mg (2.83 mmol) of linoleic acid are dissolved in 35 mL of dichloromethane. 589 mg (2.83 mmol; 1 eq.) of N,N'-dicyclohexylcarbodiimide are added. The medium is stirred for 10 min at ambient temperature, then 575 mg (2.83 mmol; 1 eq.) of compound 1 and 35 mg (283 µmol; 0.1 eq.) of 4-dimethylaminopyridine are added. The medium is stirred at ambient temperature for 48 h.

The medium is filtered through fritted glass, then the filtrate is concentrated to dryness. The residue is purified on a silica column (cyclohexane/ethyl acetate). The yield consists of 801 mg (60%) of compound 51 in the form of a colorless oil.

$^1$H NMR ($CDCl_3$, 400 MHz): δ (ppm)=0.92 (t, J=6.9 Hz, 3H); 1.34 (m, 14H); 1.70 (m, 2H); 2.08 (m, 4H); 2.12 (s, 3H); 2.45 (td, J=2.8 Hz, J=7.4 Hz, 2H); 2.8 (t, J=6.6 Hz, 2H); 2.97 (m, 2H); 3.8 (s, 3H); 5.38 (m, 5H).

UPLC-MS (AP+): 461.2 (M+H$^+$)

Example E11.2

Preparation of 2-(linoleoyloxy)-3-(methylseleno)propanoic acid (Compound 52)

Compound 52

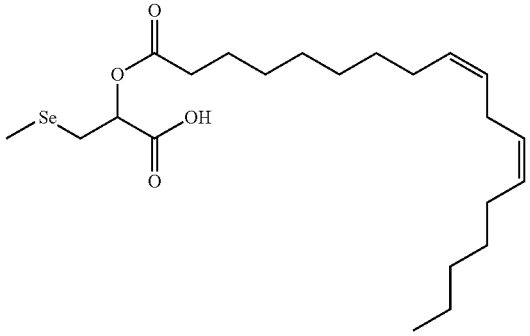

459 mg (1.59 mmol) of linoleic acid are dissolved in 19.8 mL of dichloromethane. 331 mg (2.83 mmol; 1 eq.) of N,N'-dicyclohexylcarbodiimide are added. The medium is stirred for 30 min at ambient temperature, then 300 mg (1.59 mmol; 1 eq.) of 2-hydroxy-3-(methylseleno)propanoic acid and 20 mg (159 µmol; 0.1 eq.) of 4-dimethylaminopyridine are added. The medium is stirred at ambient temperature for 24 h.

The medium is filtered through fritted glass, then the filtrate is concentrated to dryness. The residue is purified on a silica column (cyclohexane/ethyl acetate, then dichloromethane/methanol). The yield consists of 198 mg (26%) of compound 52 in the form of a colorless oil.

$^1$H NMR ($CDCl_3$, 300 MHz): δ (ppm)=0.93 (t, J=6.8 Hz, 3H); 1.35 (m, 14H); 1.70 (m, 2H); 2.1 (m, 4H); 2.15 (s, 3H); 2.45 (m, 2H); 2.8 (t, J=5.9 Hz, 2H); 3.0 (m, 2H); 5.4 (m, 5H).

UPLC-MS (AP−): 444.7 (M+H$^+$)

Example E12

Preparation of the methyl ester of 2-[(1H-imidazol-4-ylcarbonyl)oxy]-3-(methylseleno)propanoic acid (Compound 53)

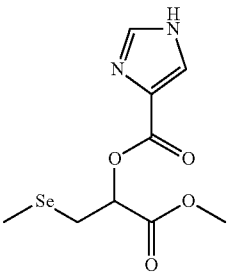

Compound 53

438 mg (3.83 mmol) of 4-imidazolecarboxylic acid are suspended in 20 mL of dichloromethane and 30 µL of N,N-dimethylformamide (383 µmol; 0.1 eq.). The medium is cooled to 0° C., then 503 µL (5.74 mmol; 1.5 eq.) of oxalyl chloride are added. The medium is cooled to 0° C. for 15 min, then stirred for 2 h at ambient temperature. The medium is concentrated to dryness.

The concentrate is redissolved in 20 mL of dichloromethane. The medium is cooled to 0° C., then 1.26 mL (7.66 mmol; 2 eq.) of N,N-diisopropylethylamine are added. 794 mg (3.83 mmol; 1 eq.) of compound 1 are added dropwise. The medium is stirred at ambient temperature for 48 h.

The medium is diluted with 50 mL of ethyl acetate, then washed with 20 mL of water. The aqueous phase is extracted with 20 mL of ethyl acetate. The organic phases are combined, washed with 20 mL of a saturated NaCl aqueous solution. The organic phase is dried with $Na_2SO_4$, filtered and concentrated. The residue is purified on a silica column (cyclohexane/ethyl acetate, then dichloromethane/methanol). The yield consists of 806 mg (70%) of compound 53 in the form of a pale yellow solid.

$^1$H NMR (DMSO, 400 MHz): δ (ppm)=2.12 (s, 3H); 3.03 (m, 21H); 3.70 (s, 3H); 5.42 (dd, J=4.6 Hz, J=7.3 Hz, 1H); 7.84 (s, 1H); 7.88 (s, 1H); 12.74 (br s, 1H).

UPLC-MS (AP+): 314.7 (M+Na$^+$)

Example E13.1

Preparation of the methyl ester of 2-(pivaloyloxy)-3-(methylseleno)propanoic acid (Compound 54)

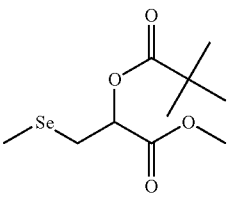

Compound 54

400 mg (1.99 mmol) of compound 1 are dissolved under nitrogen in 50 mL of dichloromethane. 1.5 g (7.95 mmol; 4 eq.) of trimethylacetic anhydride, then 24 mg (199 µmol; 0.1 eq.) of 4-dimethylaminopyridine are added to the medium. The medium is stirred under nitrogen and at ambient temperature for 48 h. 748 mg (3.98 mmol; 2 eq.) of trimethylacetic anhydride are again added to the medium. The medium is stirred under nitrogen and at ambient temperature for 96 h.

The medium is concentrated to dryness. The residue is purified on a silica column (cyclohexane/ethyl acetate). The yield consists of 484 mg (83%) of compound 54 in the form of a colorless oil.

$^1$H NMR (CDCl$_3$, 400 MHz): δ (ppm)=1.29 (s, 9H); 2.13 (s, 3H); 2.99 (m, 2H); 3.79 (s, 3H); 5.31 (dd, J=4.6 Hz, J=7.5 Hz, 1H).

UPLC-MS (AP+): 281.9 (M+H$^+$)

Example E13.2

Preparation of 2-(pivaloyloxy)-3-(methylseleno)propanoic acid (Compound 55)

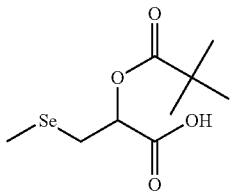

Compound 55

240 mg (0.83 mmol) of compound 54 are dissolved in 12 mL of THF. 830 µL (0.83 mmol; 1 equiv.) of a 1M lithium hydroxide aqueous solution are added, the solution is stirred at ambient temperature for 16 h. 41 µL (41 µmol, 0.05 equiv.) of a 1M lithium hydroxide aqueous solution are added, the solution is stirred at ambient temperature for 24 h.

The reaction medium is diluted in water (20 mL), then extracted with ethyl acetate (3×20 mL). The pH of the medium is adjusted to 4 by adding a 1 M hydrochloric acid aqueous solution. The medium is extracted with ethyl acetate (3×20 mL). The organic phases of this extraction are combined, dried over $Na_2SO_4$, filtered and concentrated. The yield consists of 151 mg (66%) of the desired product 55 in the form of a colorless oil.

$^1$H NMR (CDCl$_3$, 400 MHz): δ (ppm)=1.29 (s, 9H); 2.15 (s, 3H); 3.03 (m, 2H); 5.32 (dd, J=7.7 Hz, J=4.3 Hz, 1H).

UPLC-MS (AP−): 266.6 (M+H$^+$)

Example E14

Preparation of the methyl ester of 2-(3-chloropropanoyloxy)-3-(methylseleno)propanoic acid (Compound 56)

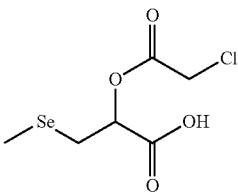

Compound 56

400 mg (1.99 mmol) of compound 1 are suspended under nitrogen in 6 mL of acetone. 324 mg (3.98 mmol; 2 eq.) of pyridine are added to the medium. The medium is cooled to −10° C., then 390 μL (3.98 mmol; 2 eq.) of 3-chloropropionyl chloride are added to the medium at −10 OC. The medium is stirred at ambient temperature for 64 h.

The reaction medium is diluted in water (20 mL), then extracted with ethyl acetate (2×20 mL). The organic phases are combined, washed with 2×20 mL of a 1M $NaHCO_3$ aqueous solution and 10 mL of a saturated NaCl aqueous solution. The organic phase is dried with $Na_2SO_4$, filtered and concentrated. The residue is purified on a silica column (cyclohexane/ethyl acetate). The yield consists of 301 mg (51%) of compound 56 in the form of a colorless oil.

$^1$H NMR ($CDCl_3$, 400 MHz): δ (ppm)=2.13 (s, 3H); 2.97 (m, 4H); 3.81 (s, 3H); 3.82 (t, J=6.6 Hz, 2H); 5.4 (dd, J=4.6 Hz, J=7.5 Hz, 1H).

Overview Table of the Preparation Examples of the Novel Compounds

| Ex. | Compound | Structure | R1 | R2 | X |
|---|---|---|---|---|---|
| A1 | 1 | 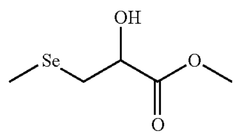 | $CH_3$ | H | $OCH_3$ |
| A2 | 1 | 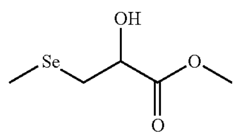 | $CH_3$ | H | $OCH_3$ |
| A3 | 2 | 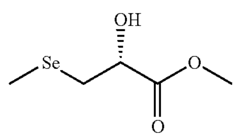 | $CH_3$ | H | $OCH_3$ |
| A4 | 3 | 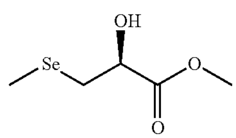 | $CH_3$ | H | $OCH_3$ |
| A5 | 4 | 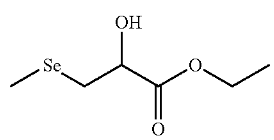 | $CH_3$ | H | $OCH_2CH_3$ |
| A6 | 5 | 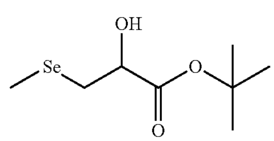 | $CH_3$ | H | $OC(CH_3)_3$ |
| A7 | 6 | 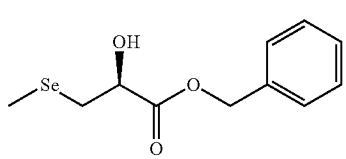 | $CH_3$ | H | $OCH_2C_6H_5$ |
| A8 | 7 | 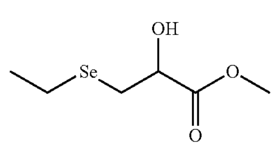 | $CH_2CH_3$ | H | $OCH_3$ |
| A9 | 8 | 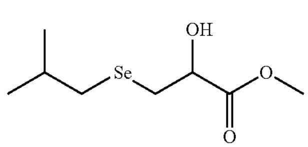 | $CH_2CH(CH_3)_2$ | H | $OCH_3$ |

-continued

| Ex. | Compound | Structure | R1 | R2 | X |
|---|---|---|---|---|---|
| A10 | 4 | (methylseleno-CH2-CH(OH)-C(O)-O-ethyl) | CH₃ | H | OCH₂CH₃ |
| A11 | 9 | (methylseleno-CH2-CH(OH)-C(O)-O-isopropyl) | CH₃ | H | OCH(CH₃)₂ |
| B1 | 10 | (methylseleno-CH2-CH(OH)-COOH) | CH₃ | H | OH |
| B2 | 10 | (methylseleno-CH2-CH(OH)-COOH) | CH₃ | H | OH |
| B3 | 11 | (methylseleno-CH2-CH(OH)-COOH, R) | CH₃ | H | OH |
| B4 | 12 | (methylseleno-CH2-CH(OH)-COOH) | CH₃ | H | OH |
| B5 | 12 | (methylseleno-CH2-CH(OH)-COOH, S) | CH₃ | H | OH |
| B6 | 13 | (ethylseleno-CH2-CH(OH)-COOH) | CH₂CH₃ | H | OH |
| B7 | 14 | (isobutylseleno-CH2-CH(OH)-COOH) | CH₂CH(CH₃)₂ | H | OH |
| C1 | 15 | (methylseleno-CH2-CH(OH)-COO⁻ · dicyclohexylammonium) | CH₃ | H | ONH₂(C₆H₁₁)₂ |

-continued

| Ex. | Compound | Structure | R1 | R2 | X |
|---|---|---|---|---|---|
| C2 | 16 | 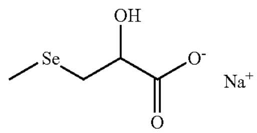 | $CH_3$ | H | Na salt |
| C3 | 17 | 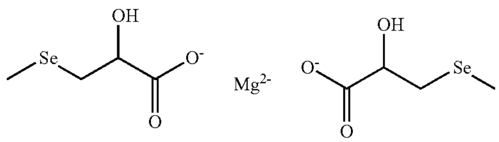 | $CH_3$ | H | Mg salt |
| C4 | 18 | 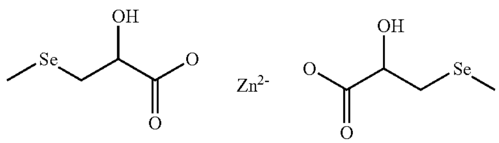 | $CH_3$ | H | Zn salt |
| C5 | 19 | 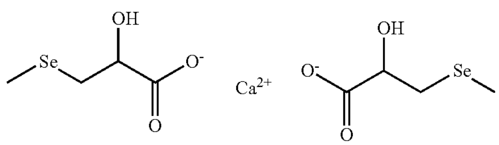 | $CH_3$ | H | Ca salt |
| D1 | 20 | 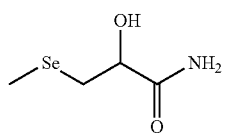 | $CH_3$ | H | $NH_2$ |
| D2 | 21 | 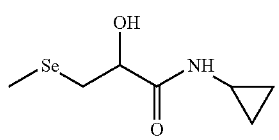 | $CH_3$ | H | $NHC_3H_5$ |
| D3 | 22 | 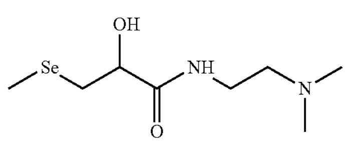 | $CH_3$ | H | $NH(CH_2)_2N(CH_3)_2$ |
| D4 | 23 | 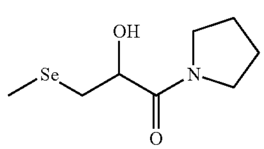 | $CH_3$ | H | $N(CH_2)_4$ |
| D5 | 24 | 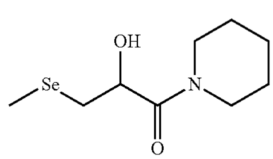 | $CH_3$ | H | $N(CH_2)_3$ |
| D6 | 25 | 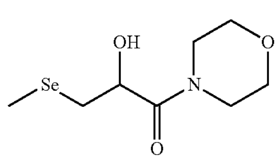 | $CH_3$ | H | $N(CH_2)_4O$ |

-continued

| Ex. | Compound | Structure | R1 | R2 | X |
|---|---|---|---|---|---|
| D7 | 26 | 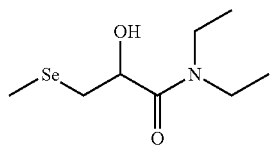 | CH₃ | H | N(C₂H₅)₂ |
| D8 | 27 | 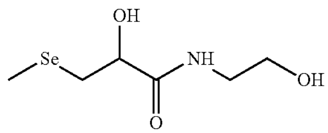 | CH₂ | H | NH(CH₂)₂OH |
| D9.1 | 28 | 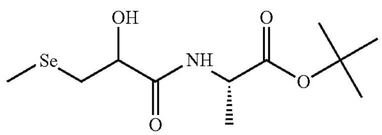 | CH₃ | H | NHAlaOC(CH₃)₃ |
| D9.2 | 29 | 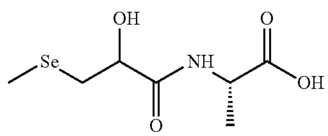 | CH₃ | H | NHAlaOH |
| D10.1 | 30 | 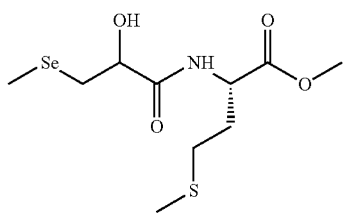 | CH₃ | H | NCHMetOCH₃ |
| D10.2 | 31 | 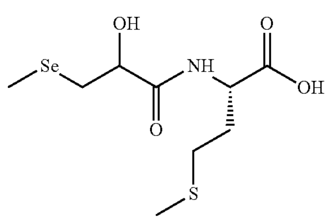 | CH₃ | H | NHMetOH |
| D11.1 | 30a | 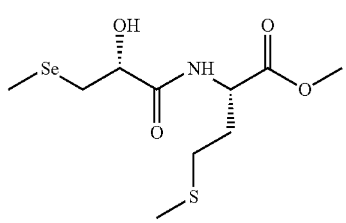 | CH₃ | H | NHMetOCH₃ |
| D11.2 | 31a | 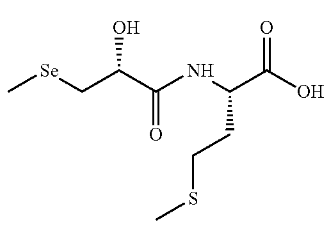 | CH₃ | H | NHMetOH |

-continued

| Ex. | Compound | Structure | R1 | R2 | X |
|---|---|---|---|---|---|
| D12.1 | 30b | 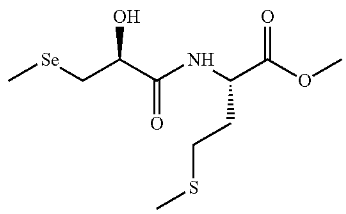 | CH₃ | H | NHMetOCH₃ |
| D12.2 | 31b | 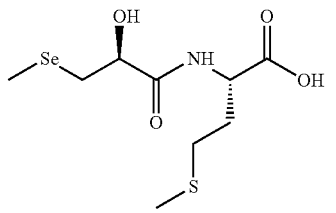 | CH₃ | H | NHMetOH |
| D13 | 32 | 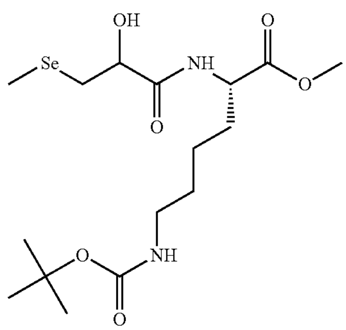 | CH₃ | H | NHLys(NHBoc)OCH₄ |
| D14 | 33 | 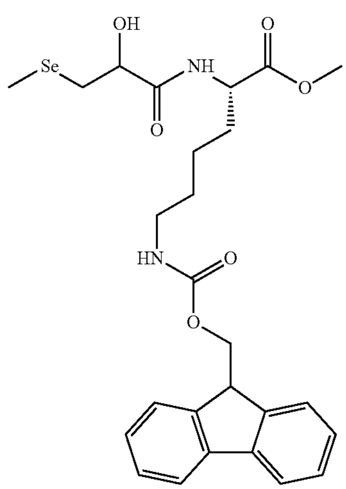 | CH₃ | H | NHLys(NHFmoc)OCH₃ |

-continued

| Ex. | Compound | Structure | R1 | R2 | X |
|---|---|---|---|---|---|
| D15 | 34 | 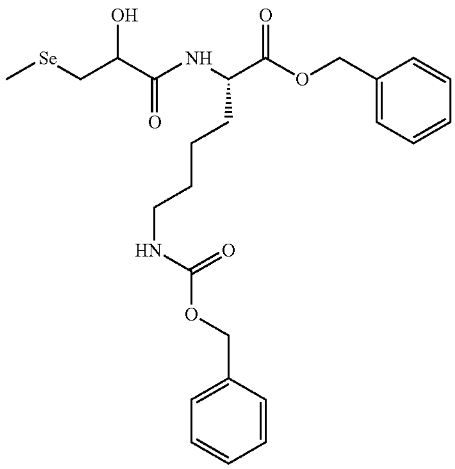 | CH$_3$ | H | NHLys(NHCbz)OCH$_2$C$_6$H$_5$ |
| D16.1 | 35 | 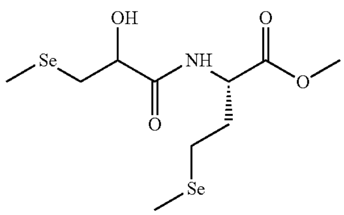 | CH$_3$ | H | NHSeMetOCH$_3$ |
| D16.2 | 36 | 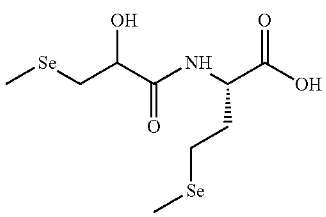 | CH$_3$ | H | NHSeMetOH |
| D17.1 | 35a | 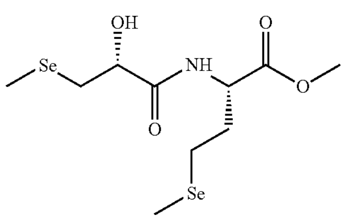 | CH$_3$ | H | NHSeMetOCH$_3$ |
| D17.2 | 36a | 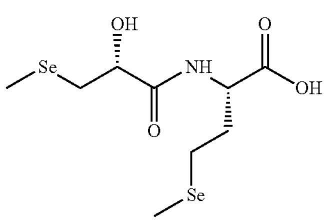 | CH$_3$ | H | NHSeMetOH |
| D18.1 | 35b | 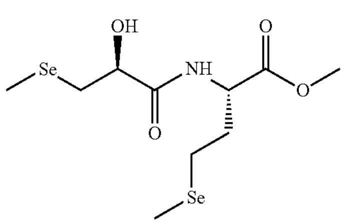 | CH$_3$ | H | NHSetMetOCH$_3$ |

-continued

| Ex. | Compound | Structure | R1 | R2 | X |
|---|---|---|---|---|---|
| D18.2 | 36b | 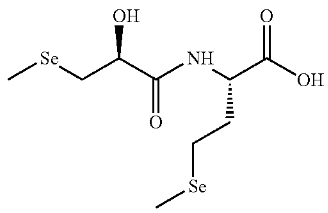 | CH$_3$ | H | NHSeMetOH |
| E1 | 37 | 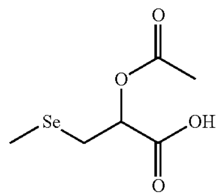 | CH$_3$ | C(=O)CH$_3$ | OH |
| E2 | 38 | 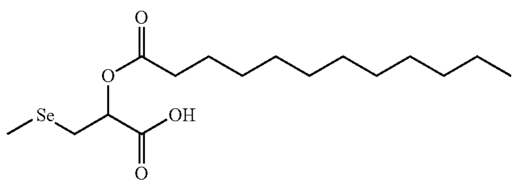 | CH$_3$ | C(=O)(CH$_2$)$_{10}$CH$_3$ | OH |
| E3.1 | 39 | 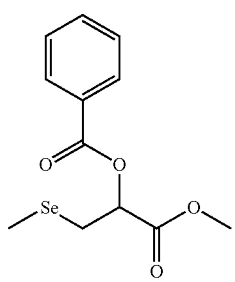 | CH$_3$ | C(=O)C$_6$H$_5$ | OCH$_3$ |
| E3.2 | 40 | 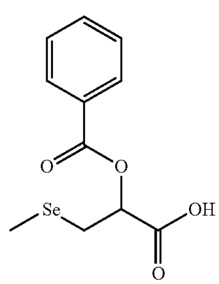 | CH$_3$ | C(=O)C$_6$H$_5$ | OH |
| E4 | 41 | 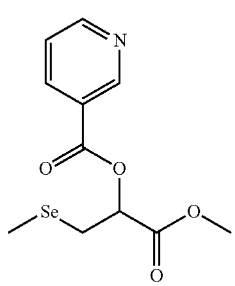 | CH$_3$ | C(=O)C$_6$H$_4$N | OCH$_3$ |

-continued

| Ex. | Compound | Structure | R1 | R2 | X |
|---|---|---|---|---|---|
| E5.1 | 42 | 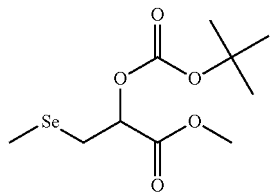 | CH$_3$ | C(=O)OC(CH$_3$)$_3$ | OCH$_3$ |
| E5.2 | 43 | 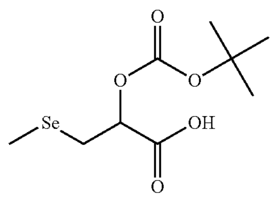 | CH$_3$ | C(=O)OC(CH$_3$)$_3$ | OH |
| E6 | 44 | 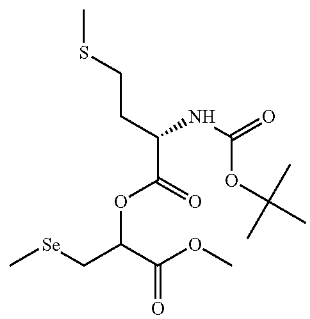 | CH$_3$ | MetNHBoc | OCH$_3$ |
| E7.1 | 45 | 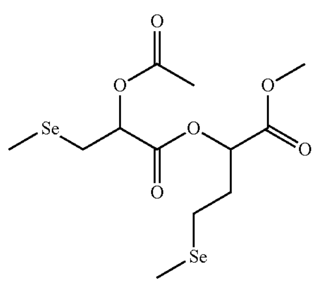 | CH$_3$ | C(=O)CH$_3$ | OSeMetOCH$_3$ |
| E7.2 | 46 | 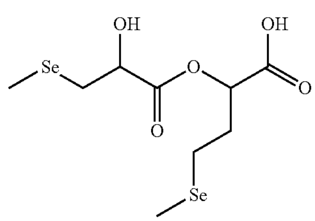 | CH$_3$ | H | OSeMetOH |
| E8.1 | 47 | 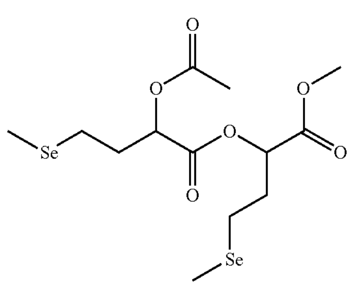 | CH$_3$ | C(=O)CH$_3$ | OSeMetOCH$_3$ |

-continued

| Ex. | Compound | Structure | R1 | R2 | X |
|---|---|---|---|---|---|
| E8.2 | 48 | 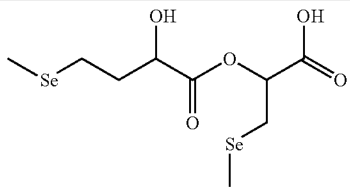 | CH$_3$ | H | OSeMetOH |
| E9 | 49 | 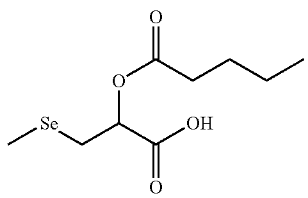 | CH$_3$ | C(=O)C$_4$H$_7$ | OH |
| E10 | 50 | 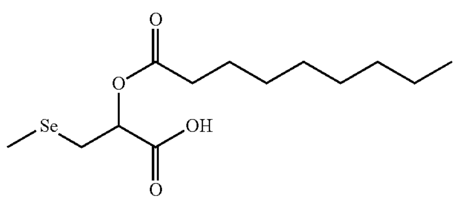 | CH$_3$ | C(=O)C$_4$H$_9$ | OH |
| E11.1 | 51 | 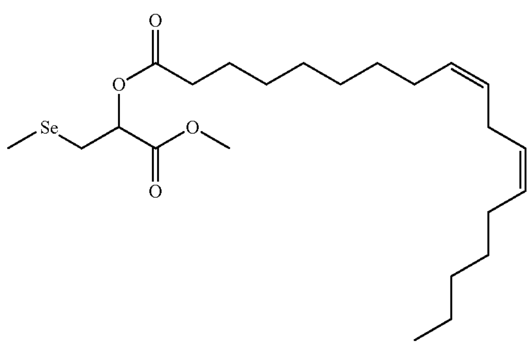 | CH$_3$ | C(=O)C$_{17}$H$_{21}$ | OCH$_3$ |
| E11.2 | 52 | 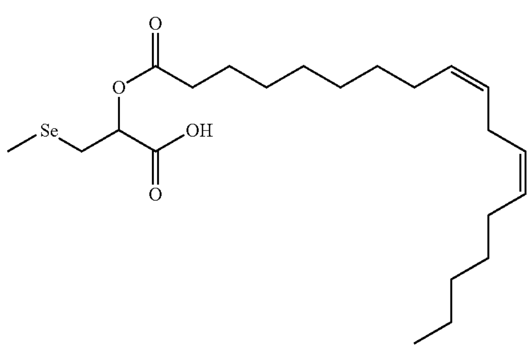 | CH$_3$ | C(=O)C$_{17}$H$_{21}$ | OH |
| E12 | 53 | 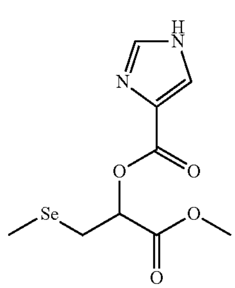 | CH$_3$ | C(=O)C$_3$H$_3$N$_2$ | OCH$_3$ |

-continued

| Ex. | Compound | Structure | R1 | R2 | X |
|---|---|---|---|---|---|
| E13.1 | 54 | (structure) | $CH_3$ | $C(=O)C(CH_3)_2$ | $OCH_3$ |
| E13.2 | 55 | (structure) | $CH_3$ | $C(=O)C(CH_3)_5$ | $OH$ |
| E14 | 56 | (structure) | $CH_3$ | $C(=O)(CH_2)_2Cl$ | $OCH_3$ |

II. Examples Describing the Antitumor Activity of the Compounds According to the Invention

II.1. Cell Lines

Eight cell lines originating from different types of cancer were used: PC3 and DU145 (prostate), HT-29 and LS-174T (colon), Hep G2 (liver), MCF-7 (breast), MIA PaCa-2 and PANC-1 (pancreas).

The characteristics of each cell line are summarized in Table I.

TABLE I

Characteristics of the cell lines used

| Organ | Cell line | Description |
|---|---|---|
| Prostate | PC3 | Adherent, human prostate adenocarcinoma grade IV derived from osseous metastasis |
| | DU145 | Adherent, human prostate carcinoma |
| Colon | HT-29 | Adherent, human adenocarcinoma (44-year old Caucasian male) |
| | LS174T | Adherent, human adenocarcinoma (58-year old Caucasian woman) |
| Liver | Hep G2 | Adherent, hepatocellular carcinoma (15-year old Caucasian) |
| Breast | MCF-7 | Adherent, human adenocarcinoma (69-year old Caucasian woman) |
| Pancreas | PANC-1 | Adherent, carcinoma (56-year old Caucasian man) |
| | MIA PaCa-2 | Adherent, carcinoma (65-year old Caucasian man) |

II.2. Culture Media

The cells are cultured in the specific culture medium described in Table II, at 37° C., 5% $CO_2$, according to the operating procedures that are well known to the person skilled in the art.

TABLE II

Composition of the culture media

| Organ | Cell line | Culture medium |
|---|---|---|
| Prostate | PC3 | RPMI 1640 + 10% FBS |
| | DU145 | RPMI 1640 + 10% FBS |
| Colon | HT-29 | McCoy's 5a + 10% FBS + 0.5 mM ultraglutamine |
| | LS174T | EMEM + 10% FBS + 2 mM ultraglutamine + 1 mM sodium pyruvate + 0.1 mM nonessential amino acids |
| Breast | MCF-7 | EMEM + 10% FBS + 2 mM ultraglutamine + 1 mM sodium pyruvate + 0.1 mM nonessential amino acids + 10 nM β-estradiol |
| Pancreas | PANC-1 | RPMI + 10% FBS |
| | MIA PaCa-2 | DMEM + 10% FBS |
| Liver | Hep G2 | EMEM + 10% of complemented FBS + 0.1 mM nonessential amino acids + 2 mM ultraglutamine + penicillin/streptomycin |

II.3. Evaluation of the Cytotoxicity of the Compounds According to the Invention After thawing and amplification of the cancer cells in the appropriate culture medium (described in 1.2.), 96-well plates are inoculated with these cells and incubated or not incubated (controls) in their respective culture medium, in the presence of the compounds to be tested at 10, 50, 100, 250 and 500 μM.

After 96 h of incubation, each 96-well plate is analyzed in order to measure the viability of the cells using a colorimetric test with WST-1.

II.4 Examples

F1. Antitumor Activity of Compound 4 (See Example A5)

The cytotoxicity results obtained with compound 4 on two cell lines are presented in FIG. 2. These results show that the viability of the cells decreases as the concentration of compound 4 increases, the concentration of decreases by 50%, the cell viability being equal to 481 and 335 µM for the cells DU145 and LS174T, respectively.

F2. Antitumor Activity of Compound 10 (See Example B1)

The cytotoxicity results obtained with compound 10 on three cell lines are presented in FIG. 3. These results show that the viability of the cells decreases as the concentration of compound 10 increases, the concentration of compound 10 decreases by 50%, the cell viability being equal to 392, 430 and 328 µM for the cells DU145, LS174T and HT-29, respectively.

F3. Antitumor Activity of Compound 38 (See Example E2)

The cytotoxicity results obtained with compound 38 on eight cell lines are presented in FIGS. 4a and 4b. These results show that the viability of the cells decreases as the concentration of compound 38 increases. The concentration of compound 38 which decreases by 50%, the cell viability is given in Table III for each cell line.

TABLE III

Concentration of compound 38 decreasing by 50% the cell viability after 96 hours of treatment

| Cell line | Compound 38 (µM) |
|---|---|
| PC3 | 198 |
| DU145 | 169 |
| PANC-1 | 253 |
| MIA PaCa-2 | 308 |
| HT-29 | 166 |
| LS174T | 113 |
| Hep G2 | 263 |
| MCF-7 | 215 |

III. Examples Describing the Compositions of the Compounds According to the Invention Example G1

Compositions Containing Compound 10

Capsules having the following composition were prepared:

| Compound 10 2-Hydroxy-3-methylselenopropanoic acid | 0.40 mg (in Se eq.) |
|---|---|
| Excipients* and envelope** (*cornstarch, lactose, magnesium stearate, flavor, **gelatin, titanium dioxide, dyes) | a 1000 mg capsule |

Example G2

Compositions Containing Compound 38

Capsules having the following composition were prepared:

| Compound 38 2-(Dodecanoyloxy)-3-(methylseleno) propanoic acid | 0.40 mg (in Se eq.) |
|---|---|
| Excipients* and envelope** (*cornstarch, lactose, magnesium stearate, flavor, **gelatin, titanium dioxide, dyes) | a 1000 mg capsule |

Example G3

Compositions Containing Compound 10 and Compound 38

Capsules having the following compositions were prepared:

| Compound 10 2-Hydroxy-3-methylselenopropanoic acid | 0.10 mg (in Se eq.) |
|---|---|
| Compound 38 2-(Dodecanoyloxy)-3-(methylseleno)propanoic acid | 0.40 mg (in Se eq.) |
| Excipients* and envelope** (*cornstarch, lactose, magnesium stearate, flavor, **gelatin, titanium dioxide, dyes) | a 1000 mg capsule |

The invention claimed is:

1. A selenium compound having the following general formula (I):

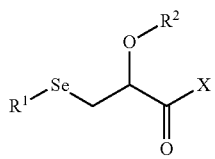

GENERAL FORMULA (I)

where
$R^1$=a radical selected from a non substituted linear, branched or cyclic saturated carbon containing radical with 1 to 26 carbon atoms, and a substituted linear, branched or cyclic saturated carbon containing radical with 1 to 26 carbon atoms which is substituted by at least one substituent selected from the group consisting of one or more fluorine atoms, one or more carbon-carbon double bonds, at least one OH group, and at least one amino group;
$R^2$=H, $R^4C(=O)$, $R^4OC(=O)$, α-aminoacyl, $CH_3SeCH_2CH_2CH(NH_2)C(=O)$, $CH_3SeCH_2CH_2CH(OH)C(=O)$;
X=OH, $OR^3$, $NH_2$, $NR^4R^5$, α-amino acid, $CH_3SeCH_2CH_2CH(COOH)NH-$, $CH_3SeCH_2CH_2CH(COOH)O-$;
$R^3$=alkyl;
$R^4$=alkyl, aryl;
$R^5$=H, alkyl, aryl;
$R^4$ and $R^5$ being capable of forming together a 5- or 6-membered cycloalkyl radical which can comprise a heteroatom;
provided that X≠NH-tert-butyl, and any stereoisomers or the pharmaceutically accepted acid or base salts thereof.

2. The selenium compound according to claim 1, wherein $R^1$ represents a methyl, ethyl, or allyl group.

3. The selenium compound according to claim 1, wherein $R^2$ is selected from the group consisting of H, α-aminoacyls, $R^4(C=O)$, $R^4O(C=O)$, and $CH_3SeCH_2CH_2CH(OH)C(=O)$.

4. The selenium compound according to claim 1, wherein X is selected from the group consisting OH, α-amino acid, $CH_3SeCH_2CH_2CH(COOH)NH-$, and $CH_3SeCH_2CH_2CH(COOH)O-$.

5. The selenium compound according to claim 1, wherein $R^1$ represents a methyl, ethyl, or allyl group; $R^2$ represents $R^4(C=O)$, or $R^4O(C=O)$, and X represents OH or $OR^3$.

6. The selenium compound according to claim 1, wherein the pharmaceutically acceptable acids are selected from mineral acids comprising hydrochloric, hydrobromic, hydroiodic, sulfuric, and phosphoric acids, or selected from organic acids comprising formic, acetic, trifluoroacetic, propionic, tartaric, benzoic, maleic, fumaric, succinic, citric, oxalic, glyoxylic, and aspartic acids, alkanesulfonic acids comprising methanesulfonic, trifluoromethanesulfonic, and ethanesulfonic, and arylsulfonic acids comprising benzene- and paratoluenesulfonic acids.

7. The selenium compound according to claim 1, wherein the pharmaceutically acceptable bases are selected from mineral bases comprising sodium, lithium, calcium, potassium, magnesium, ammonium or zinc hydroxides, carbonates of alkali or alkaline earth metals comprising sodium, lithium, calcium, potassium, magnesium, ammonium or zinc carbonates and bicarbonates, or organic bases comprising methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, proceine, lysine, arginine, histidine, and N-methylglucamine, or else phosphonium salts comprising the alkyl-phosphonium salts, the aryl-phosphonium salts, the alkyl-aryl-phosphonium salts, and the alkenyl-aryl-phosphonium salts, or quaternary ammonium salts.

8. The selenium compound according to claim 1, wherein said compound is selected from the group consisting of:
2-hydroxy-3-(methylseleno)propanoic acid methyl ester;
(R)-2-hydroxy-3-(methylseleno)propanoic acid methyl ester;
(S)-2-hydroxy-3-(methylseleno)propanoic acid methyl ester;
2-hydroxy-3-(methylseleno)propanoic acid ethyl ester;
(S)-(2-hydroxy-3-(methylseleno)propanoic acid benzyl ester;
3-(ethylseleno)-2-hydroxypropanoic acid methyl ester;
2-hydroxy-3-(isobutylseleno)propanoic acid methyl ester;
2-hydroxy-3-(methylseleno)propanoic acid isopropyl ester;
2-hydroxy-3-(methylseleno)propanoic acid;
(R)-2-hydroxy-3-(methylseleno)propanoic acid;
(S)-2-hydroxy-3-(methylseleno)propanoic acid;
3-ethylseleno-2-hydroxypropanoic acid;
2-hydroxy-3-(isobutylseleno)propanoic acid;
dicyclohexylammonium 2-hydroxy-3-(methylseleno)propanoate salt;
sodium 2-hydroxy-3-(methylseleno)propanoate salt;
magnesium bis(2-hydroxy-3-(methylseleno)propanoate salt;
zinc bis(2-hydroxy-3-(methylseleno)propanoate salt;
calcium bis(2-hydroxy-3-(methylseleno)propanoate salt;
2-hydroxy-3-(methylseleno)propanamide;
N-cyclopropyl-2-hydroxy-3-(methylseleno)propanamide;
N-[2-(dimethylamino)ethyl]-2-hydroxy-3-(methylseleno)propanamide;
2-hydroxy-3-(methylseleno)-1-(pyrrolidin-1-yl)propan-1-one;
2-hydroxy-3-(methylseleno)-1-(piperidin-1-yl)propan-1-one;
2-hydroxy-3-(methylseleno)-1-(morpholin-4-yl)propan-1-one;
N, N-diethyl-2-hydroxy-3-(methylseleno)propanamide;
2-hydroxy-N-(2-hydroxyethyl)-3-(methylseleno)propanamide;
[(2RS)-2-hydroxy-3-methylselenopropanoyl]-(S)-alanine;
[(2RS)-2-hydroxy-3-methylselenopropanoyl]-(S)-methionine methyl ester;
[(2RS)-2-hydroxy-3-methylselenopropanoyl]-(S)-methionine;
[(2R)-2-hydroxy-3-methylselenopropanoyl]-(S)-methionine methyl ester;
[(2R)-2-hydroxy-3-methylselenopropanoyl]-(S)-methionine;
[(2S)-2-hydroxy-3-methylselenopropanoyl]-(S)-methionine methyl ester;
[(2S)-2-hydroxy-3-methylselenopropanoyl]-(S)-methionine;
N($\alpha$)-[(2RS)-2-hydroxy-3-methylselenopropanoyl]-N($\omega$)-tert-butoxycarbonyl-(S)-lysine methyl ester;
N($\alpha$)-[(2RS)-2-hydroxy-3-methylselenopropanoyl]-N($\omega$)-fluorenylmethyloxycarbonyl-(S)-lysine methyl ester;
N($\alpha$)-[(2 RS)-2-hydroxy-3-methylselenopropanoyl]-N($\omega$)-benzyloxycarbonyl-(S)-lysine methyl ester;
[(2RS)-2-hydroxy-3-methylselenopropanoyl]-(S)-selenomethionine methyl ester;
[(2RS)-2-hydroxy-3-methylselenopropanoyl]-(S)-selenomethionine;
[(2R)-2-hydroxy-3-methylselenopropanoyl]-(S)-selenomethionine methyl ester;
[(2R)-2-hydroxy-3-methylselenopropanoyl]-(S)-selenomethionine;
[(2S)-2-hydroxy-3-methylselenopropanoyl]-(S)-selenomethionine methyl ester;
[(2S)-2-hydroxy-3-methylselenopropanoyl]-(S)-selenomethionine;
2-(acetyloxy)-3-(methylseleno)propanoic acid;
2-(dodecanoyloxy)-3-(methylseleno)propanoic acid;
2-(benzoyloxy)-3-(methylseleno)propanoic acid methyl ester;
2-(benzoyloxy)-3-(methylseleno)propanoic acid;
3-(methylseleno)-2-[(3'-pyridine)oxycarbonyl]propanoic acid methyl ester;
2-[(tert-butoxycarbonyl)oxy]-3-(methylseleno)propanoic acid methyl ester;
2-[(tert-butoxycarbonyl)oxy]-3-(methylseleno)propanoic acid;
(2RS)—[N-(tert-butoxycarbonyl)-S-methionyl]-3-(methylseleno)propanoic acid methyl ester;
4-methylseleno-2-(2'-acetyloxy-3'-methylselenopropanoyl)butyric acid methyl ester;
4-methylseleno-2-(2'-acetyloxy-3'-methylselenopropanoyl)butyric acid;
3-methylseleno-2-(2'-acetoxy-4'-methylselenobutanoyl) propanoic acid methyl ester;
3-methylseleno-2-(2'-hydroxy-4'-methylselenobutanoyl) propanoic acid;
2-(pentanoyloxy)-3-(methylseleno)propanoic acid;
2-(nonanoyloxy)-3-(methylseleno)propanoic acid;
2-(linoleoyloxy)-3-(methylseleno)propanoic acid;
2-(linoleoyloxy)-3-(methylseleno)propanoic acid methyl ester;
2-(pivaloyloxy)-3-(methylseleno)propanoic acid;
2-(3-chloropropanoyloxy)-3-(methylseleno)propanoic acid;
2-{(1H-imidazoyl-4-ylcarbonyl)oxy)}-3-(methylseleno) propanoic acid;
2-(pivaloyloxy)-3-(methylseleno)propanoic acid methyl ester.

9. A method for preparing the selenium compounds of general formula (I), defined in claim 1, wherein it includes the following steps:

a) the reaction of a racemic (DL) oxirane-2-carboxylic acid ester or of one of the enantiomers thereof (D or L) which are commercially available, with:
either an alkylselenol $R^1SeH$, which is itself prepared in situ from an alkali metal salt of alkylselenolate of formula $R^1$—Se-$M_1$ which is itself obtained by reduction of dialkyl diselenide where $M_1$ represents an alkali metal atom), which is reacted with ammonium chloride;
or a dialkylaluminum alkylselenolate derivative of formula $Al(R^1)_2SeR^1$, which is itself generated in situ from the corresponding trialkylaluminum $Al(R^1)_3$ and elemental selenium Se(0),
b) if applicable, one or more of the following reactions or series of reactions:
hydrolysis of the ester function, then
acidification of the reaction medium in order to obtain the corresponding acids of formula (I) where X=OH; then
esterification of the acids of formula (I) or of the alkali metal salts thereof with an alcohol or an alkyl halide in order to obtain the corresponding esters of general formula (I) where X=$OR^3$, with $R^3$ as defined above;
amidification of the acids of formula (I) with an appropriate amine of formula $R^4R^5NH$ or $NH_3$ where $R^5$ is as defined above, in order to obtain the compound of general formula (I) where X=$NH_2$, $NR^4R^5$ or α-amino acid, $CH_3SeCH_2CH_2CH(COOH)NH$—,
esterification, when $R^2$=H, of the hydroxyl function by an appropriate acid in order to obtain the compound of general formula (I) where $OR^2$ is different from the OH group;
salification by an acid or by a base.

10. The method according to claim 9, wherein the selenium reagent is:
either a dialkylaluminum alkylselenolate, in an aprotic polar solvent;
or an alkylselenol, generated in situ from metal selenium Se(0) and alkyl lithium, in an aprotic polar solvent, and then put in the presence of ammonium chloride.

11. The method according to claim 9, wherein reaction 1) takes place in an aprotic polar solvent, and in that the subsequent reactions leading to the different compounds of formula (I) include at least one acidification, or esterification, or amidification and salification.

12. A method of carrying out treatment of tumors or cancers comprising:
providing at least one selenium compound of formula (I) as defined in claim 1 as a pharmaceutical agent alone or combined with at least one other agent selected from at least one other pharmaceutical agent and at least one other antitumor agent, and
carrying out a treatment of the tumors or cancers using the pharmaceutical agent alone or combined with at least one other agent selected from at least one other pharmaceutical agent and at least one other antitumor agent.

13. A pharmaceutical composition, wherein it includes at least one pharmaceutically active ingredient including at least one selenium compound of general formula (I) as defined in claim 1, alone or combined with at least one other pharmaceutically active ingredient.

14. The pharmaceutical composition according to claim 13, wherein the selenium compound of general formula (I) constitutes a pharmaceutically active ingredient for carrying out the treatment of tumors or cancers selected from the group consisting of tumors or cancers of the prostate, of the liver, of the pancreas, of the breast, and of the colon, either alone or in combination with one or more other known anticancer or cytotoxic agents, either by pre-administration or by co-administration.

15. The pharmaceutical composition according to claim 13, wherein at least one of the other anticancer agents is selected from the following compounds:
aminoglutethimide, estramustine, medroxyprogesterone acetate, leuprolide, flutamide, toremifene, matrix metalloproteinase inhibitors; VEGF inhibitors selected from the group comprising anti-VEGF antibodies (Avastin (R)) and the small molecules selected from the group comprising ZD6474 and SU6668, vatalanib, BAY-43-9006, SU11248, CP-547632 and CEP-7055, the SA-1 and SA-2 inhibitors selected from the group comprising the anti-HER2 antibodies (Herceptin), EGFR inhibitors selected from the group comprising gefitinib, erlotinib, ABX-EGF, EMD72000, 11F8, and cetuximab, Eg5 inhibitors selected from the group comprising SB-715992, SB-743921, and MKI-833; PAN inhibitors selected from the group comprising canertinib, EKB-569, CI-1033, AEE-788, and XL-647; kinase inhibitors selected from the group comprising 2C4, and GW-572016, dasatinib, bicalutamide, tamoxifen, MAPK kinase inhibitors, PI3 kinase inhibitors, PDGF inhibitors selected from the group comprising imatinib, anti-angiogenic agents and the antivascular agents, receptor and non-receptor tyrosine kinase inhibitors, inhibitors of integrin signaling; tubulin, anticancer agents selected from the group comprising vinblastine, vincristine, vinorelbine, vinflunine, paclitaxel, docetaxel, 7-O-methylthiomethylpaclitaxel, 4-deacetyl-4-methylcarbonatepaclitaxel, C-4 methyl carbonate paclitaxel, epothilone A, epothilone B, epothilone C, epothilone D, deoxyepothilone A, deoxyepothilone B, oxabicyclo[14.1.0]-heptadecane-5-9-dione (ixabepilone), leucovorin, tegafur, CDK inhibitors, antiproliferative cell cycle inhibitors, epidophyllotoxin, etoposide, VM-26; anti-neoplastic enzymes, topoisomerase I or II inhibitors selected from the group comprising camptothecin, topotecan, SN-38, procarbazine, mitoxantrone; platinum coordination complexes selected from the group comprising cisplatin, carboplatin and oxaliplatin, purine antagonists selected from the group comprising 6-thioguanine and 6-mercaptopurine, and glutamine antagonists.

16. The pharmaceutical composition according to claim 13, wherein at least one of the other cytotoxic agents is selected from at least one compound that follows: cyclophosphamide, doxorubicin, daunorubicin, mitoxantrone, melphalan, hexamethyl melamine, thiotepa, cytarabine, idatrexate, trimetrexate, dacarbazine, L-asparaginase, bicalutamide, leuprolide, pyridobenzoindole derivatives, the interferons, the interleukins.

17. The pharmaceutical composition according to claim 13, wherein it includes at least one selenium compound of formula (I) at a concentration between 0.02% and 0.15% by weight in selenium equivalent.

18. The pharmaceutical composition according to claim 13, wherein it includes at least one pharmaceutically acceptable carrier and a therapeutically effective amount of one or more of the selenium compounds selected from the group consisting of a selenium compound as defined in claim 1, of a stereoisomer thereof, of a tautomer thereof, and of a pharmaceutically acceptable salt thereof, said carrier consisting essentially of:

an injectable or drinkable solution, a solid medium composed of one or more excipients which are selected from the group consisting of vitamins, natural antioxidants, L-ergothioneine, mineral salts, mono-, di- or polysaccharides, folic acid, vitamins $B_6$, vitamin E, vitamin C, lactose, starch.

19. The pharmaceutical composition according to claim 13, wherein it is formulated for a route of administration selected from the oral route, intravenous route, parenteral route, topical route selected from a transdermal route, a nasal route, an ocular route, and inhalation.

20. The pharmaceutical composition according to claim 13, wherein said at least one selenium compound of formula (I) is selected from the group consisting of

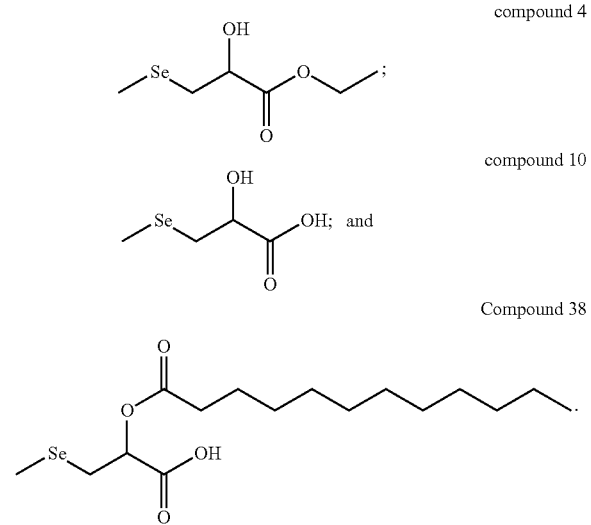

21. The pharmaceutical composition according to claim 20, wherein said at least one selenium compound of formula (I) is incorporated in an effective amount to treat a tumor or cancer selected from the group consisting of a tumor or cancer of the prostate, a tumor or cancer of the liver, a tumor or cancer of the pancreas, a tumor or cancer of the breast, and a tumor or cancer of the colon.

22. The method of claim 12, wherein said at least one selenium compound of formula (I) is selected from the group consisting of

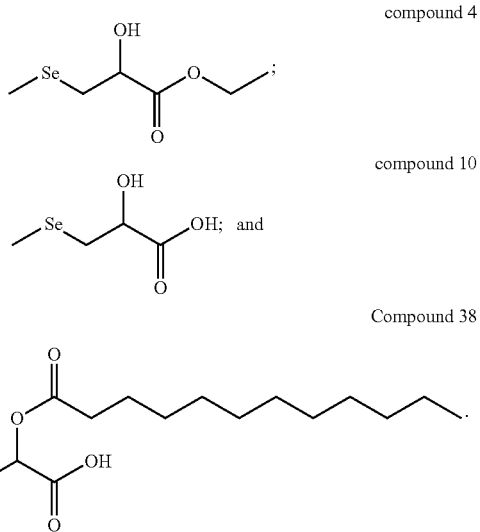

23. The method according to claim 22, wherein said at least one selenium compound of formula (I) is incorporated in an effective amount to treat a tumor or cancer selected from the group consisting of a tumor or cancer of the prostate, a tumor or cancer of the liver, a tumor or cancer of the pancreas, a tumor or cancer of the breast, and a tumor or cancer of the colon.

* * * * *